US009776757B2

(12) United States Patent
McKinnon et al.

(10) Patent No.: US 9,776,757 B2
(45) Date of Patent: Oct. 3, 2017

(54) SYRINGE LABELING DEVICE

(71) Applicant: Becton, Dickinson and Company, Franklin Lakes, NJ (US)

(72) Inventors: Austin Jason McKinnon, Herriman, UT (US); Scott William Gisler, Washingtonville, NY (US); Philip C. McNeill, Tarrytown, NY (US); Rahul Khurana, Hackensack, NJ (US); Drew Davidock, Newton, NJ (US); Robert Nicholas Graf, Morristown, NJ (US); Kaushal Verma, Somerset, NJ (US); Gary Stacey, Cambridge (GB); Mark Rogers, Swaffham Bulbeck (GB); Mark Ridley, Cambridge (GB); David Stocks, Fowlmere (GB); Alistair Ward, Cambridge (GB); Andrew Scholan, Cambridge (GB); Keith Marshall, Cambridge (GB)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/878,478

(22) Filed: Oct. 8, 2015

(65) Prior Publication Data
US 2016/0101887 A1   Apr. 14, 2016

Related U.S. Application Data

(60) Provisional application No. 62/062,266, filed on Oct. 10, 2014.

(51) Int. Cl.
*B29C 65/48* (2006.01)
*B32B 37/10* (2006.01)
(Continued)

(52) U.S. Cl.
CPC .............. *B65C 3/16* (2013.01); *A61M 5/178* (2013.01); *A61M 5/31* (2013.01); *B65C 9/06* (2013.01);
(Continued)

(58) Field of Classification Search
USPC ... 156/363, DIG. 3, DIG. 6, DIG. 8, DIG. 9, 156/DIG. 11, DIG. 14, DIG. 26, DIG. 27,
(Continued)

(56) References Cited

U.S. PATENT DOCUMENTS 607,941 A   7/1898   Mayo
614,703 A   11/1898   Delory
(Continued)

FOREIGN PATENT DOCUMENTS

GB   2183046 B   5/1987
GB   2504288 A   1/2014
(Continued)

OTHER PUBLICATIONS

English abstract of JP 11-326337 (Feb. 22, 2017).*
(Continued)

*Primary Examiner* — Sing P Chan
(74) *Attorney, Agent, or Firm* — The Webb Law Firm

(57) ABSTRACT

A labeling device for a syringe that includes a first labeling subsystem adapted to print a first label having machine readable information and a second labeling subsystem adapted to print a second label having human readable information is disclosed. The first labeling subsystem includes a label applicator adapted to automatically apply the first label to a portion of the syringe. The first labeling subsystem includes a syringe clamp assembly that securely holds the syringe while the label applicator automatically applies a first label to the syringe. The second labeling
(Continued)

subsystem includes a removal device adapted to automatically remove a backing material from the second label.

17 Claims, 23 Drawing Sheets

(51) Int. Cl.
| | |
|---|---|
| *B32B 37/12* | (2006.01) |
| *B32B 38/14* | (2006.01) |
| *B32B 38/18* | (2006.01) |
| *B32B 39/00* | (2006.01) |
| *B32B 41/00* | (2006.01) |
| *B32B 43/00* | (2006.01) |
| *B65C 9/04* | (2006.01) |
| *B65C 9/06* | (2006.01) |
| *B65C 9/26* | (2006.01) |
| *B65C 9/40* | (2006.01) |
| *B65C 3/16* | (2006.01) |
| *A61M 5/31* | (2006.01) |
| *B65C 9/30* | (2006.01) |
| *A61M 5/178* | (2006.01) |
| *B65C 9/46* | (2006.01) |

(52) U.S. Cl.
CPC .............. *B65C 9/30* (2013.01); *B65C 9/46* (2013.01); *A61M 2005/3125* (2013.01); *A61M 2207/00* (2013.01)

(58) Field of Classification Search
USPC .................................... 156/DIG. 39, DIG. 47
See application file for complete search history.

(56) References Cited

U.S. PATENT DOCUMENTS

| | | | |
|---|---|---|---|
| 3,430,625 | A | 3/1969 | McLeod, Jr. |
| 4,003,252 | A | 1/1977 | Dewath |
| 4,349,405 | A * | 9/1982 | Dudzik .................... B65C 3/14 156/358 |
| 4,415,802 | A | 11/1983 | Long |
| 4,853,521 | A | 8/1989 | Claeys et al. |
| 4,857,713 | A | 8/1989 | Brown |
| 4,921,277 | A | 5/1990 | McDonough |
| 4,978,335 | A | 12/1990 | Arthur, III |
| 5,040,422 | A | 8/1991 | Frankenberger et al. |
| 5,078,683 | A | 1/1992 | Sancoff et al. |
| 5,179,862 | A | 1/1993 | Lynnworth |
| 5,247,826 | A | 9/1993 | Frola et al. |
| 5,317,506 | A | 5/1994 | Coutre et al. |
| 5,429,602 | A | 7/1995 | Hauser |
| 5,463,906 | A | 11/1995 | Spani et al. |
| 5,531,697 | A | 7/1996 | Olsen et al. |
| 5,531,698 | A | 7/1996 | Olsen |
| 5,569,212 | A | 10/1996 | Brown |
| 5,611,784 | A | 3/1997 | Barresi et al. |
| 5,612,524 | A | 3/1997 | Sant'Anselmo et al. |
| 5,624,402 | A * | 4/1997 | Imbert ................ A61M 5/3134 604/111 |
| 5,628,309 | A | 5/1997 | Brown |
| 5,651,775 | A | 7/1997 | Walker et al. |
| 5,692,640 | A | 12/1997 | Caulfield et al. |
| 5,720,733 | A | 2/1998 | Brown |
| 5,740,428 | A | 4/1998 | Mortimore et al. |
| 5,782,814 | A | 7/1998 | Brown et al. |
| 5,792,117 | A | 8/1998 | Brown |
| 5,845,264 | A | 12/1998 | Nellhaus |
| 5,873,731 | A | 2/1999 | Prendergast |
| 5,882,338 | A | 3/1999 | Gray |
| 5,925,014 | A | 7/1999 | Teeple, Jr. |
| 6,106,498 | A | 8/2000 | Friedli et al. |
| 6,123,686 | A | 9/2000 | Olsen et al. |
| D438,634 | S | 3/2001 | Merry |
| 6,249,299 | B1 | 6/2001 | Tainer |
| 6,256,037 | B1 | 7/2001 | Callahan |
| 6,341,174 | B1 | 1/2002 | Callahan et al. |
| 6,342,889 | B1 | 1/2002 | Callahan |
| 6,381,029 | B1 | 4/2002 | Tipirneni |
| 6,422,094 | B1 | 7/2002 | Ganshorn |
| 6,464,667 | B1 | 10/2002 | Kamen et al. |
| 6,482,185 | B1 | 11/2002 | Hartmann |
| 6,519,569 | B1 | 2/2003 | White et al. |
| RE38,189 | E | 7/2003 | Walker et al. |
| 6,626,355 | B2 | 9/2003 | Sasse et al. |
| 6,641,562 | B1 | 11/2003 | Peterson |
| 6,644,130 | B2 | 11/2003 | Imai et al. |
| 6,675,660 | B1 | 1/2004 | Mosier et al. |
| 6,685,227 | B2 | 2/2004 | Merry et al. |
| 6,685,678 | B2 | 2/2004 | Evans et al. |
| 6,697,067 | B1 | 2/2004 | Callahan et al. |
| 6,733,495 | B1 | 5/2004 | Bek et al. |
| 6,742,992 | B2 | 6/2004 | Davis |
| 6,798,533 | B2 | 9/2004 | Tipirneni |
| 6,825,864 | B2 | 11/2004 | Botten et al. |
| 6,854,338 | B2 | 2/2005 | Khuri-Yakub et al. |
| 6,985,870 | B2 | 1/2006 | Martucci et al. |
| 7,000,485 | B2 | 2/2006 | Ao et al. |
| 7,074,209 | B2 | 7/2006 | Evans et al. |
| 7,106,479 | B2 | 9/2006 | Roy et al. |
| 7,115,113 | B2 | 10/2006 | Evans et al. |
| 7,116,343 | B2 | 10/2006 | Botten et al. |
| 7,161,488 | B2 | 1/2007 | Frasch |
| 7,175,081 | B2 | 2/2007 | Andreasson et al. |
| 7,180,624 | B2 | 2/2007 | Tipirneni |
| 7,182,256 | B2 | 2/2007 | Andreasson et al. |
| 7,225,683 | B2 | 6/2007 | Harnett et al. |
| 7,236,936 | B2 | 6/2007 | White et al. |
| 7,237,199 | B1 | 6/2007 | Menhardt et al. |
| 7,264,323 | B2 | 9/2007 | Tainer et al. |
| 7,299,981 | B2 | 11/2007 | Hickle et al. |
| 7,319,540 | B2 | 1/2008 | Tipirneni |
| 7,347,841 | B2 | 3/2008 | Elhadad et al. |
| 7,358,505 | B2 | 4/2008 | Woodworth et al. |
| 7,360,448 | B2 | 4/2008 | Maginnis et al. |
| 7,375,737 | B2 | 5/2008 | Botten et al. |
| 7,442,181 | B2 | 10/2008 | Schubert et al. |
| 7,469,598 | B2 | 12/2008 | Shkarlet et al. |
| 7,469,599 | B2 | 12/2008 | Froehlich et al. |
| D588,200 | S | 3/2009 | Langan et al. |
| 7,534,239 | B1 | 5/2009 | Schneider et al. |
| D593,613 | S | 6/2009 | Langan et al. |
| D595,361 | S | 6/2009 | Langan et al. |
| 7,559,483 | B2 | 7/2009 | Hickle et al. |
| 7,564,579 | B2 | 7/2009 | Tipirneni |
| D597,608 | S | 8/2009 | Langan et al. |
| D602,534 | S | 10/2009 | Langan et al. |
| 7,614,545 | B2 | 11/2009 | Christoffersen et al. |
| 7,617,739 | B1 | 11/2009 | Dam |
| D605,228 | S | 12/2009 | Langan et al. |
| D605,229 | S | 12/2009 | Langan et al. |
| D605,230 | S | 12/2009 | Langan et al. |
| 7,645,258 | B2 | 1/2010 | White et al. |
| 7,673,527 | B2 | 3/2010 | Ehring et al. |
| 7,694,565 | B2 | 4/2010 | Koerdt et al. |
| 7,703,336 | B2 | 4/2010 | Genosar |
| 7,704,231 | B2 | 4/2010 | Pongpairochana et al. |
| 7,753,880 | B2 | 7/2010 | Malackowski |
| 7,753,891 | B2 | 7/2010 | Tennican et al. |
| 7,756,724 | B2 | 7/2010 | Gropper et al. |
| 7,763,006 | B2 | 7/2010 | Tennican |
| D621,879 | S | 8/2010 | Langan et al. |
| D621,880 | S | 8/2010 | Langan et al. |
| 7,776,018 | B2 | 8/2010 | Bush, Jr. et al. |
| D624,595 | S | 9/2010 | Langan et al. |
| D624,596 | S | 9/2010 | Langan et al. |
| 7,799,010 | B2 | 9/2010 | Tennican |
| 7,815,123 | B2 | 10/2010 | Conner et al. |
| 7,815,605 | B2 | 10/2010 | Souter |
| 7,819,838 | B2 | 10/2010 | Ziegler et al. |
| 7,822,096 | B2 | 10/2010 | Kuksenkov |
| 7,859,473 | B2 | 12/2010 | Gibson |
| D633,151 | S | 2/2011 | Langan et al. |

(56) References Cited

U.S. PATENT DOCUMENTS

| | | |
|---|---|---|
| 7,887,513 B2 | 2/2011 | Nemoto et al. |
| D634,367 S | 3/2011 | Langan et al. |
| D634,368 S | 3/2011 | Langan et al. |
| D634,369 S | 3/2011 | Langan et al. |
| 7,905,861 B2 | 3/2011 | Rhinehart et al. |
| 7,918,830 B2 | 4/2011 | Langan et al. |
| 7,927,313 B2 | 4/2011 | Stewart et al. |
| 7,933,780 B2 | 4/2011 | De La Huerga |
| 7,941,949 B2 | 5/2011 | Cloninger |
| D639,861 S | 6/2011 | Langan et al. |
| D639,862 S | 6/2011 | Langan et al. |
| D639,863 S | 6/2011 | Langan et al. |
| 7,967,778 B2 | 6/2011 | Nemoto et al. |
| D641,421 S | 7/2011 | Langan et al. |
| D641,422 S | 7/2011 | Langan et al. |
| 7,976,508 B2 | 7/2011 | Hoag |
| D643,468 S | 8/2011 | Langan et al. |
| D643,469 S | 8/2011 | Langan et al. |
| D643,470 S | 8/2011 | Langan et al. |
| D643,471 S | 8/2011 | Langan et al. |
| D643,472 S | 8/2011 | Langan et al. |
| 7,991,627 B2 | 8/2011 | Hutchinson et al. |
| D645,094 S | 9/2011 | Langan et al. |
| 8,031,347 B2 | 10/2011 | Edwards et al. |
| D649,196 S | 11/2011 | Langan et al. |
| 8,059,297 B2 | 11/2011 | Tipirneni |
| 8,063,925 B2 | 11/2011 | Tainer et al. |
| 8,065,924 B2 | 11/2011 | Ziegler et al. |
| 8,069,060 B2 | 11/2011 | Tipirneni |
| 8,111,159 B2 | 2/2012 | Andreasson et al. |
| 8,140,349 B2 | 3/2012 | Hanson et al. |
| 8,235,938 B2 | 8/2012 | Eggers et al. |
| 8,328,082 B1 | 12/2012 | Bochenko et al. |
| 8,355,753 B2 | 1/2013 | Bochenko et al. |
| 8,385,972 B2 | 2/2013 | Bochenko et al. |
| 8,394,053 B2 | 3/2013 | Bochenko et al. |
| 8,494,093 B1 | 7/2013 | Zhang |
| 8,582,171 B2 | 11/2013 | Srnka et al. |
| 8,606,596 B1 | 12/2013 | Bochenko et al. |
| 8,639,525 B2 | 1/2014 | Levine et al. |
| 8,702,674 B2 | 4/2014 | Bochenko |
| 8,752,088 B1 | 6/2014 | Harvey et al. |
| 8,945,066 B2 | 2/2015 | Bochenko et al. |
| 9,039,655 B2 | 5/2015 | Prince et al. |
| 9,078,809 B2 | 7/2015 | Bochenko et al. |
| 9,101,534 B2 | 8/2015 | Bochenko |
| 2001/0020148 A1 | 9/2001 | Sasse et al. |
| 2001/0049608 A1 | 12/2001 | Hochman |
| 2001/0056258 A1 | 12/2001 | Evans |
| 2002/0020459 A1 | 2/2002 | Baldwin et al. |
| 2002/0040208 A1 | 4/2002 | Flaherty et al. |
| 2002/0099334 A1 | 7/2002 | Hanson et al. |
| 2002/0188259 A1 | 12/2002 | Hickle et al. |
| 2003/0055685 A1 | 3/2003 | Cobb et al. |
| 2003/0135388 A1 | 7/2003 | Martucci et al. |
| 2003/0139701 A1 | 7/2003 | White et al. |
| 2003/0160698 A1 | 8/2003 | Andreasson et al. |
| 2003/0164401 A1 | 9/2003 | Andreasson et al. |
| 2004/0082918 A1 | 4/2004 | Evans et al. |
| 2004/0105115 A1 | 6/2004 | Edwards et al. |
| 2004/0179051 A1 | 9/2004 | Tainer et al. |
| 2004/0179132 A1 | 9/2004 | Fujino et al. |
| 2004/0193453 A1 | 9/2004 | Butterfield et al. |
| 2004/0212834 A1 | 10/2004 | Edwards et al. |
| 2004/0238631 A1 | 12/2004 | Andreasson et al. |
| 2005/0070978 A1 | 3/2005 | Bek et al. |
| 2005/0088306 A1 | 4/2005 | Andreasson et al. |
| 2005/0101905 A1 | 5/2005 | Merry |
| 2005/0118048 A1 | 6/2005 | Traxinger |
| 2005/0151652 A1 | 7/2005 | Frasch |
| 2005/0151823 A1 | 7/2005 | Botten et al. |
| 2005/0154368 A1 | 7/2005 | Lim et al. |
| 2005/0277873 A1 | 12/2005 | Stewart et al. |
| 2005/0277890 A1 | 12/2005 | Stewart et al. |
| 2006/0032918 A1 | 2/2006 | Andreasson et al. |
| 2006/0037709 A1* | 2/2006 | Itoh .................. B65C 9/32 156/446 |
| 2006/0065713 A1 | 3/2006 | Kingery |
| 2006/0079843 A1 | 4/2006 | Brooks et al. |
| 2006/0102503 A1 | 5/2006 | Elhadad et al. |
| 2006/0143051 A1 | 6/2006 | Eggers et al. |
| 2006/0144942 A1 | 7/2006 | Evans et al. |
| 2006/0178617 A1 | 8/2006 | Adams et al. |
| 2006/0190302 A1 | 8/2006 | Eggers et al. |
| 2006/0206356 A1 | 9/2006 | Vanderveen |
| 2006/0224125 A1 | 10/2006 | Simpson et al. |
| 2006/0229551 A1 | 10/2006 | Martinez et al. |
| 2006/0270997 A1 | 11/2006 | Lim et al. |
| 2006/0287887 A1 | 12/2006 | Hutchinson et al. |
| 2007/0008399 A1 | 1/2007 | Botten et al. |
| 2007/0029032 A1 | 2/2007 | McCarthy et al. |
| 2007/0100316 A1 | 5/2007 | Traxinger |
| 2007/0134044 A1 | 6/2007 | Colbrunn et al. |
| 2007/0167919 A1 | 7/2007 | Nemoto et al. |
| 2007/0179448 A1 | 8/2007 | Lim et al. |
| 2007/0187475 A1 | 8/2007 | MacLeod |
| 2007/0191787 A1 | 8/2007 | Lim et al. |
| 2007/0255199 A1 | 11/2007 | Dewey |
| 2007/0280710 A1 | 12/2007 | Tainer et al. |
| 2007/0293830 A1 | 12/2007 | Martin |
| 2008/0043088 A1 | 2/2008 | Botten et al. |
| 2008/0071219 A1 | 3/2008 | Rhinehart et al. |
| 2008/0118141 A1 | 5/2008 | Sommer et al. |
| 2008/0191013 A1 | 8/2008 | Liberatore |
| 2008/0243088 A1 | 10/2008 | Evans |
| 2008/0255523 A1 | 10/2008 | Grinberg |
| 2008/0294108 A1 | 11/2008 | Briones et al. |
| 2008/0306439 A1 | 12/2008 | Nelson et al. |
| 2009/0018494 A1 | 1/2009 | Nemoto et al. |
| 2009/0043253 A1 | 2/2009 | Podaima |
| 2009/0067973 A1* | 3/2009 | Eliuk .................. B66C 1/42 414/729 |
| 2009/0112178 A1 | 4/2009 | Behzadi |
| 2009/0112333 A1 | 4/2009 | Sahai |
| 2009/0126866 A1 | 5/2009 | Stenner et al. |
| 2009/0137956 A1 | 5/2009 | Souter |
| 2009/0143673 A1 | 6/2009 | Drost et al. |
| 2009/0149744 A1 | 6/2009 | Nemoto et al. |
| 2009/0156931 A1 | 6/2009 | Nemoto et al. |
| 2009/0159654 A1 | 6/2009 | Grimard |
| 2009/0198208 A1* | 8/2009 | Stavsky .............. A61J 1/2096 604/407 |
| 2009/0200185 A1 | 8/2009 | Follman et al. |
| 2009/0259176 A1 | 10/2009 | Yairi |
| 2009/0288497 A1 | 11/2009 | Ziegler et al. |
| 2009/0296540 A1 | 12/2009 | Gilbert et al. |
| 2009/0306620 A1 | 12/2009 | Thilly et al. |
| 2010/0022953 A1 | 1/2010 | Bochenko et al. |
| 2010/0022987 A1 | 1/2010 | Bochenko et al. |
| 2010/0036310 A1 | 2/2010 | Hillman |
| 2010/0036313 A1 | 2/2010 | Shener et al. |
| 2010/0065633 A1 | 3/2010 | Nelson et al. |
| 2010/0076310 A1 | 3/2010 | Wenderow et al. |
| 2010/0095782 A1 | 4/2010 | Ferencz et al. |
| 2010/0114951 A1 | 5/2010 | Bauman et al. |
| 2010/0145165 A1 | 6/2010 | Merry |
| 2010/0204659 A1 | 8/2010 | Bochenko et al. |
| 2010/0280486 A1 | 11/2010 | Khair et al. |
| 2010/0286599 A1 | 11/2010 | Ziegler et al. |
| 2010/0305499 A1 | 12/2010 | Matsiev et al. |
| 2011/0009800 A1 | 1/2011 | Dam et al. |
| 2011/0009817 A1 | 1/2011 | Bennett et al. |
| 2011/0028937 A1 | 2/2011 | Powers et al. |
| 2011/0060198 A1 | 3/2011 | Bennett et al. |
| 2011/0111794 A1 | 5/2011 | Bochenko et al. |
| 2011/0112473 A1 | 5/2011 | Bochenko et al. |
| 2011/0112474 A1 | 5/2011 | Bochenko et al. |
| 2011/0137288 A1 | 6/2011 | Tallarida et al. |
| 2011/0152824 A1 | 6/2011 | DiPerna et al. |
| 2011/0152825 A1 | 6/2011 | Marggi |
| 2011/0152834 A1 | 6/2011 | Langan et al. |
| 2011/0161112 A1 | 6/2011 | Keefe et al. |
| 2011/0166511 A1 | 7/2011 | Sharvit et al. |
| 2011/0185821 A1 | 8/2011 | Genosar |

(56) References Cited

U.S. PATENT DOCUMENTS

| | | |
|---|---|---|
| 2011/0259954 A1 | 10/2011 | Bartz et al. |
| 2011/0264069 A1 | 10/2011 | Bochenko |
| 2011/0315611 A1 | 12/2011 | Fulkerson et al. |
| 2012/0004602 A1 | 1/2012 | Hanson et al. |
| 2012/0004637 A1 | 1/2012 | Krulevitch et al. |
| 2012/0006127 A1 | 1/2012 | Nielsen |
| 2012/0022458 A1 | 1/2012 | Oh et al. |
| 2012/0035535 A1 | 2/2012 | Johnson et al. |
| 2012/0037266 A1 | 2/2012 | Bochenko |
| 2012/0046295 A1 | 2/2012 | Charrier et al. |
| 2012/0065617 A1 | 3/2012 | Matsiev et al. |
| 2012/0286533 A1* | 11/2012 | Mettler ............... B25J 19/023 294/213 |
| 2012/0287431 A1 | 11/2012 | Matsiev et al. |
| 2012/0323208 A1 | 12/2012 | Bochenko et al. |
| 2012/0325330 A1 | 12/2012 | Prince et al. |
| 2013/0006415 A1* | 1/2013 | Paydar ............... G06F 19/3462 700/235 |
| 2013/0018356 A1 | 1/2013 | Prince et al. |
| 2015/0204705 A1 | 7/2015 | Forster et al. |
| 2015/0211904 A1 | 7/2015 | Forster |

FOREIGN PATENT DOCUMENTS

| | | | |
|---|---|---|---|
| GB | 2504295 A | | 1/2014 |
| GB | 2504297 A | | 1/2014 |
| JP | 04154534 A | * | 5/1992 |
| JP | 11326337 A | * | 11/1999 |
| JP | 2008302934 A | * | 12/2008 |
| WO | 0170304 A1 | | 9/2001 |
| WO | 0211787 A2 | | 2/2002 |
| WO | 2005089833 A1 | | 9/2005 |
| WO | 2009114115 A1 | | 9/2009 |
| WO | 2010144482 A2 | | 12/2010 |
| WO | 2012034084 A2 | | 3/2012 |
| WO | 2014016311 A1 | | 1/2014 |
| WO | 2014016315 A1 | | 1/2014 |
| WO | 2014016316 A1 | | 1/2014 |

OTHER PUBLICATIONS

English abtract of JP 2008-3202934 (Feb. 22, 2017).*
English abstract of JP 04-154534 (Feb. 22, 2017).*
Machine translation of JP 11-326337 (Feb. 22, 2017).*
Machine translation of JP 2008-302934 (Feb. 22, 2017).*
Machine translation of JP 04-154534 (Feb. 22, 2017).*

* cited by examiner

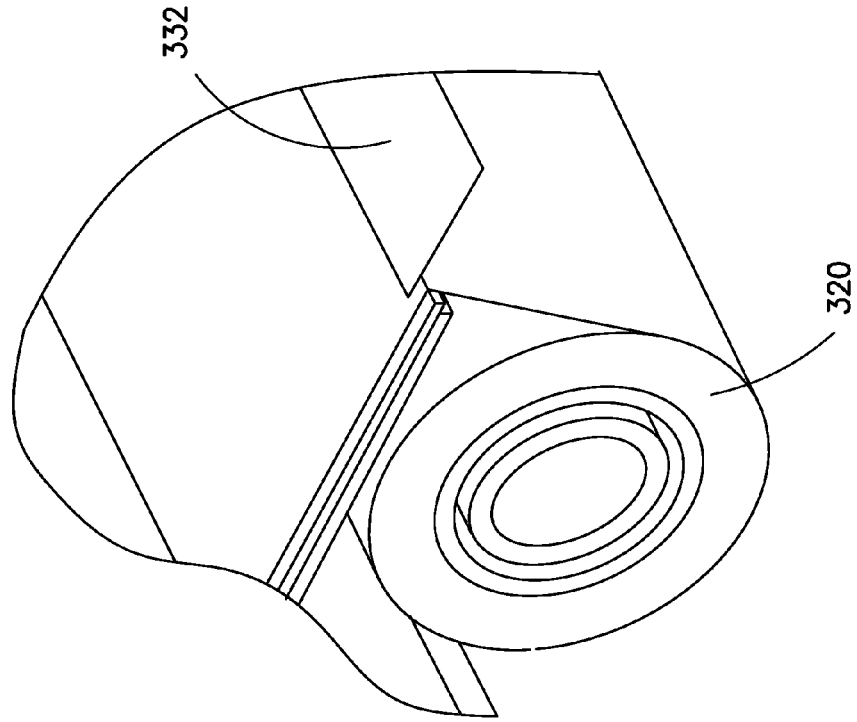
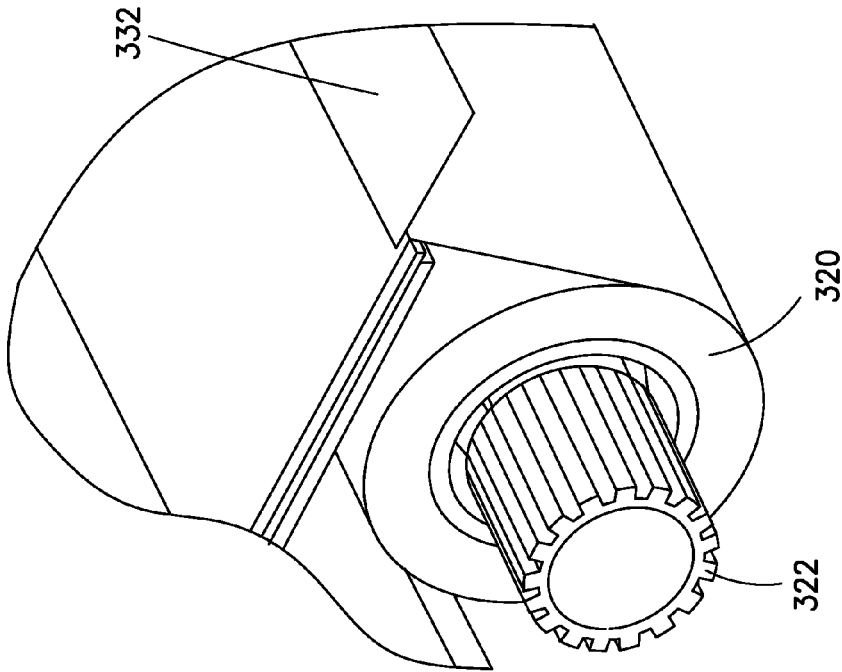

SYRINGE LABELING DEVICE

CROSS-REFERENCE TO RELATED APPLICATION

The present application claims priority to U.S. Provisional Application Ser. No. 62/062,266, filed Oct. 10, 2014, entitled "Syringe Labeling Device", the entire disclosure of which is hereby incorporated by reference.

BACKGROUND OF THE INVENTION

1. Field of the Disclosure

The present disclosure relates generally to a labeling device for a syringe. More particularly, the present disclosure relates to a labeling device for a syringe that prints a first label having machine readable information and a second label having human readable information.

2. Description of the Related Art

Syringes need to include information to help medical professionals identify the contents of the syringes. Errors such as giving an incorrect medication or an incorrect dose can easily be made if the contents of the syringe cannot be positively identified from the point of time that a medication is transferred to a syringe up to the moment of its administration.

The results of missed and unintended medication include adverse effects to patients and significant costs to the healthcare industry. Potential causes for these errors include unclear syringe contents due to unlabeled or poorly labeled syringes and poor record keeping of which drugs were administered and the concentration and quantity of the administered drug.

Identifying the content of a syringe based on the appearance of that content is unreliable. Visual identification of the medication is very difficult since several of the medications are identical or nearly identical in appearance.

SUMMARY OF THE INVENTION

The present disclosure provides a labeling device for a syringe that includes a first labeling subsystem adapted to print a first label having machine readable information and a second labeling subsystem adapted to print a second label having human readable information. The first labeling subsystem includes a label applicator adapted to automatically apply the first label to a portion of the syringe. The first labeling subsystem includes a syringe clamp assembly that securely holds the syringe while the label applicator automatically applies a, first label to the syringe. The second labeling subsystem includes a removal device adapted to automatically remove a backing material from the second label.

In accordance with an embodiment of the present invention, a labeling device for a syringe includes a first labeling subsystem adapted to print a first label comprising machine readable information and a second labeling subsystem adapted to print a second label comprising human readable information.

In one configuration, the first labeling subsystem includes a label applicator adapted to automatically apply the first label to a portion of the syringe. In another configuration, the first labeling subsystem includes a first printer adapted to print the first label. In yet another configuration, the second labeling subsystem includes a second printer adapted to print the second label.

In accordance with another embodiment of the present invention, a labeling device for a syringe includes a first labeling subsystem having a clamp assembly adapted to hold the syringe; a first printer adapted to print a first label comprising machine readable information; and a label applicator assembly adapted to automatically apply the first label to a portion of the syringe; a second labeling subsystem having a second printer adapted to print a second label comprising human readable information; and a removal device adapted to automatically remove a backing material from the second label.

In one configuration, the labeling device further includes a scanner adapted to scan a container having a medication therein to retrieve medication information for the medication contained in the container. In another configuration, the labeling device further includes a touchscreen interface adapted to display the medication information. In yet another configuration, the labeling device further includes a database adapted to store information for a plurality of different medications. In one configuration, the database is stored in the labeling device.

In accordance with another embodiment of the present invention, a labeling subsystem for a labeling device for a syringe includes a clamp assembly adapted to hold the syringe; a printer adapted to print a first label comprising machine readable information; and a label applicator assembly adapted to automatically apply the first label to a portion of the syringe.

In one configuration, the clamp assembly includes a plurality of jaws movable between an open position and a closed position in which the jaws hold the syringe. In another configuration, with the plurality of jaws in the closed position, the clamp assembly is adapted to rotate the syringe while the label applicator assembly automatically applies the first label to a portion of the syringe. In yet another configuration, the clamp assembly includes a drive gear and movement of the jaws between the open position and the closed position is controlled by a movable cam connection between the jaws and the drive gear. In one configuration, the clamp assembly includes a holding element adapted to provide a gripping surface to pick up the clamp assembly. In another configuration, the clamp assembly includes a syringe alignment component adapted to position the syringe within the clamp assembly. In yet another configuration, the labeling subsystem further includes a print and apply state controller that activates the printer to print the first label and activates the label applicator assembly to automatically apply the first label to a portion of the syringe. In one configuration, the label applicator assembly includes an optical syringe alignment unit having a first camera for locating a precise position of the syringe within the clamp assembly and a second camera for inspecting the machine readable information on the first label. In another configuration, the label applicator assembly includes a pinch roller mechanism for exerting a force on the first label as the first label is automatically applied to the syringe to ensure that the first label is securely applied to the syringe.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 20 is a first detailed, perspective view of a removal device of a second labeling subsystem in accordance with an embodiment of the present invention.

FIG. 21 is a second detailed, perspective view of a removal device of a second labeling subsystem in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
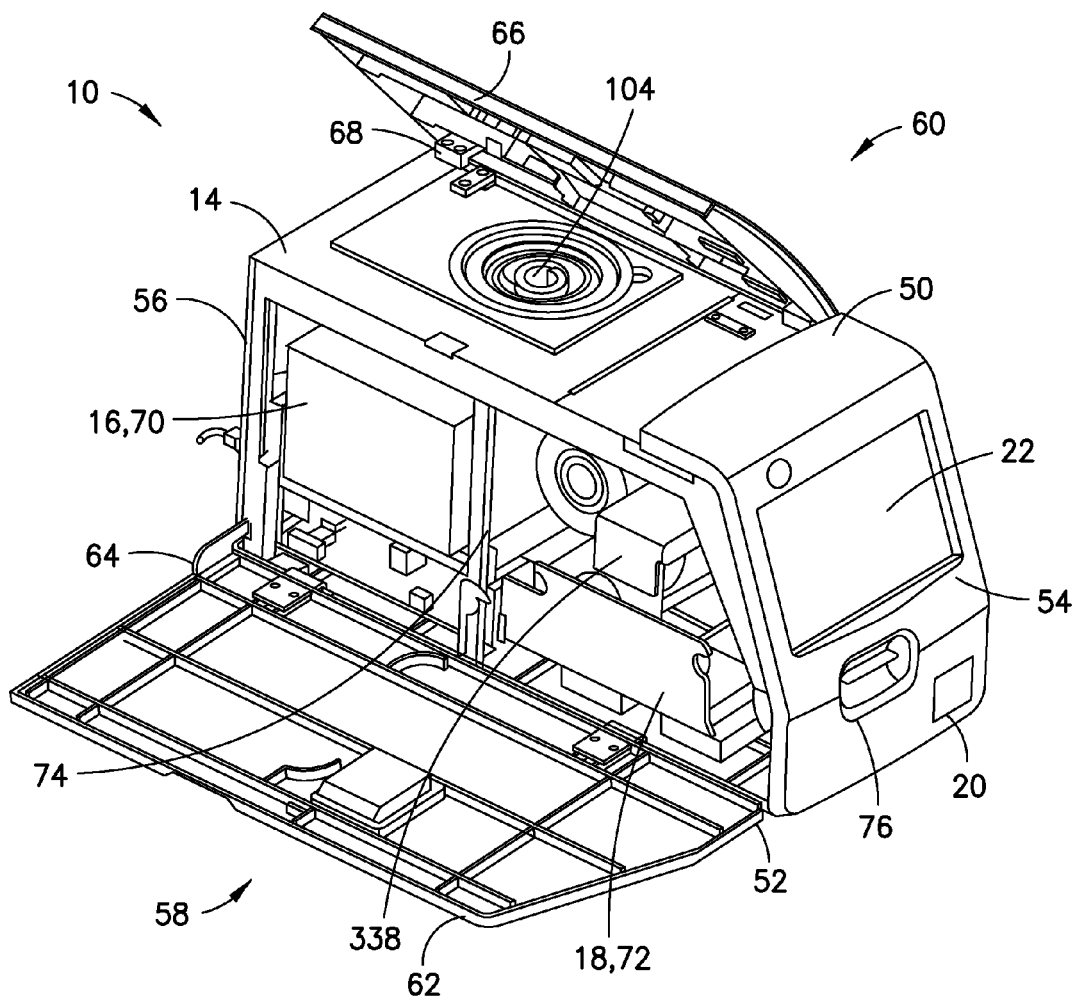
FIG. 1 is a perspective view of a labeling device with a top door and a side door in an open position in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

FIGS. 1-21 illustrate an exemplary embodiment of the present disclosure. Referring to FIGS. 1-21, a labeling device 10 for a syringe 12 includes a housing 14, a first labeling subsystem 16, a tensioning control device or second labeling subsystem 18, a scanner 20, and a touchscreen interface 22 as will be described in more detail below. Labeling device 10 provides an encoded syringe labeler for the labeling of syringes in a medical setting such as an operating room, pharmacy, or perioperative space of a hospital.

Labeling device 10 is compatible with a plurality of different syringes. For example, labeling device 10 is compatible with any syringe available from Becton, Dickinson and Company of Franklin Lakes, N.J. In one embodiment, labeling device 10 is compatible with any luer lock syringe available from Becton, Dickinson and Company of Franklin Lakes, N.J.

Figure 2A:
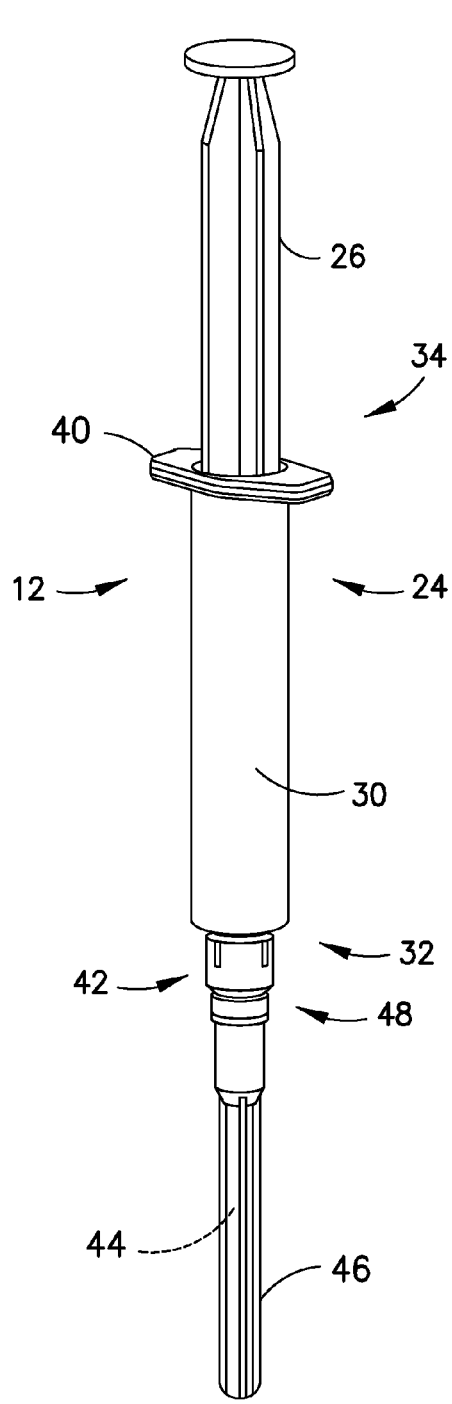
FIG. 2A is a perspective view of a syringe with a needle attached to the syringe and a protective cap covering the needle in accordance with an embodiment of the present invention.
Figure 2B:
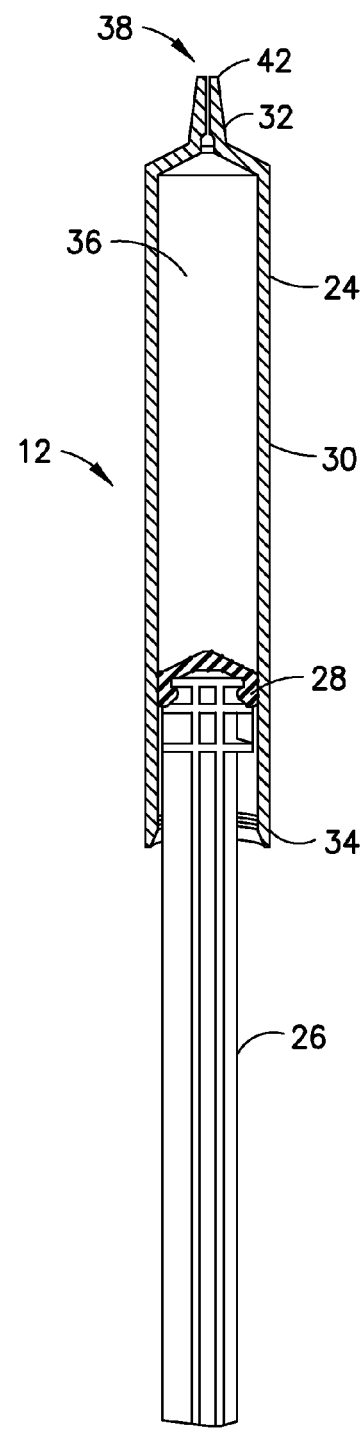
FIG. 2B is a cross-sectional view of a syringe barrel, stopper, and plunger rod of a syringe in accordance with an embodiment of the present invention.

Referring to FIGS. 2A and 2B, in one embodiment, syringe 12 includes a syringe barrel 24, a plunger rod 26, a stopper 28, a needle 44, and a protective cap 46. Syringe 12 may be adapted for the dispensing and delivery of a fluid and/or collection of a fluid. For example, syringe 12 may be used for injection or infusion of fluid such as a medication into a patient. Syringe 12 is contemplated for use in connection with a needle, such as by connecting syringe 12 to a separate needle assembly such as needle 44, or alternatively for connection with an intravenous (IV) connection assembly (not shown). It can be appreciated that the present disclosure can be used with any type of syringe assembly.

Referring to FIGS. 2A and 2B, syringe barrel 24 generally includes a barrel body or sidewall 30 extending between a first or distal end 32 and a second or proximal end 34. Sidewall 30 defines an elongate aperture or interior chamber 36 of syringe barrel 24. In one embodiment, interior chamber 36 may span the extent of syringe barrel 24 so that syringe barrel 24 is cannulated along its entire length. In one embodiment, syringe barrel 24 may be in the general form of an elongated cylindrical barrel as is known in the art in the general shape of a hypodermic syringe. In alternative embodiments, syringe barrel 24 may be in other forms for containing a fluid for delivery, such as in the general form of an elongated rectangular barrel, for example. Syringe barrel 24 may be formed of glass, or may be injection molded from thermoplastic material such as polypropylene and polyethylene according to techniques known to those of ordinary skill in the art, though it is to be appreciated that syringe barrel 24 may be made from other suitable materials and according to other applicable techniques. In certain configurations, syringe barrel 24 may include an outwardly extending flange 40 about at least a portion of proximal end 34. Flange 40 may be configured for easy grasping by a medical practitioner.

Distal end 32 of syringe barrel 24 includes an outlet opening 38 which is in fluid communication with chamber 36. Outlet opening 38 may be sized and adapted for engagement with a separate device, such as a needle assembly or IV connection assembly and, therefore, may include a mechanism for such engagement as is conventionally known. In one embodiment, distal end 32 may include a generally-tapered luer tip 42 for engagement with an optional separate tapered luer structure of such a separate device for attachment therewith such as needle 44. In one configuration, both the tapered luer tip 42 and the separate tapered luer structure may be provided with syringe 12. In such a configuration, the separate tapered luer structure may be fitted with an attachment mechanism, such as a threaded engagement, for corresponding engagement with a separate device such as needle 44. In another configuration, tapered luer tip 42 may be provided for direct engagement with a separate device such as needle 44. In one embodiment, needle 44 includes a needle hub 48 for engagement to distal end 32 of syringe barrel 24. In addition, a mechanism for locking engagement therebetween may also be provided with at least one of tapered luer tip 42 and/or the separate tapered luer structure, such as a luer collar or luer lock including interior threads. Such luer connections and luer locking mechanisms are well known in the art.

Proximal end 34 of syringe barrel 24 is generally open-ended, but is intended to be closed off to the external environment as discussed herein. Syringe barrel 24 may also include markings, such as graduations located on sidewall 30, for providing an indication as to the level or amount of fluid contained within interior chamber 36 of syringe barrel 24. Such markings may be provided on an external surface of sidewall 30, an internal surface of sidewall 30, or integrally formed or otherwise within sidewall 30 of syringe barrel 24. In other embodiments, alternatively, or in addition thereto, the markings may also provide a description of the contents of the syringe or other identifying information as may be known in the art, such as maximum and/or minimum fill lines.

In some embodiments, syringe 12 may be useful as a pre-filled syringe, and, therefore, may be provided for end use with a fluid, such as a medication or drug, contained within interior chamber 36 of syringe barrel 24, pre-filled by the manufacturer. In this manner, syringe 12 can be manufactured, pre-filled with a medication, sterilized, and packaged in appropriate packaging for delivery, storage, and use by the end user. In such embodiments, syringe 12 may include a sealing cap member disposed at distal end 32 of syringe barrel 24 to seal a fluid, such as a medication, within interior chamber 36 of syringe barrel 24.

Referring to FIG. 2B, syringe 12 includes stopper 28 which is moveably or slidably disposed within interior chamber 36, and in sealing contact with the internal surface of sidewall 30 of syringe barrel 24, thereby separating interior chamber 36 into a proximal chamber adjacent proximal end 34, and a distal chamber adjacent distal end 32. Stopper 28 is sized relative to syringe barrel 24 to provide sealing engagement with the interior surface of sidewall 30 of syringe barrel 24. Additionally, stopper 28 may include one or more annular ribs extending around the periphery of stopper 28 to increase the sealing engagement between stopper 28 and the interior surface of sidewall 30 of syringe barrel 24. In alternate embodiments, a singular O-ring or a plurality of O-rings may be circumferentially disposed about stopper 28 to increase the sealing engagement with the interior surface of sidewall 30.

Referring to FIGS. 2A and 2B, syringe 12 further includes plunger rod 26 which provides a mechanism for dispensing fluid contained within interior chamber 36 of syringe barrel 24 through outlet opening 38 upon connection of plunger rod 26 to syringe barrel 24 via stopper 28. Plunger rod 26 is adapted for advancing stopper 28. In one embodiment, plunger rod 26 is sized for movement within interior chamber 36 of syringe barrel 24.

Referring to FIG. 2A, syringe barrel 24 includes a needle 44 attached. The needle 44 is used to fill the syringe barrel 24 with a medication from a separate container, such as a vial, prior to use. In one embodiment, needle 44 is a blunt needle. The protective cap 46 is attached to the syringe barrel 24 to surround and cover the needle 44 to prevent accidental needle stick injuries.

Labeling device 10 provides an encoded syringe labeler for the labeling of syringes in a medical setting such as an operating room, pharmacy, or perioperative space of a hospital. Referring to FIG. 1, the labeling device 10 for a syringe 12 includes a housing 14, a first labeling subsystem 16, a second labeling subsystem 18, a scanner 20, and a touchscreen interface 22. The housing 14 of labeling device 10 generally includes a top portion 50, a bottom portion 52, a front portion 54, a rear portion 56, a first side portion 58, and a second side portion 60. The labeling device 10 includes a side door 62 located at first side portion 58. In one embodiment, side door 62 may be connected to first side portion 58 of housing 14 by a hinged portion 64. In this manner, side door 62 may be transitioned between a closed position and an open position as shown in FIG. 1.

The labeling device 10 includes a top door 66 located at top portion 50. In one embodiment, top door 66 may be connected to top portion 50 of housing 14 by a hinged portion 68. In this manner, top door 66 may be transitioned between a closed position and an open position as shown in FIG. 1.

The labeling device 10 includes a label slot or opening 76 located at front portion 54 of housing 14 of labeling device 10. The label slot 76 provides an exit portion for a second label 300 having human readable information 302 as described in more detail below, and shown in FIG. 2C.

In one embodiment, the scanner 20 is located on front portion 54 of housing 14 of labeling device 10. The scanner 20 is adapted to scan a portion of a container having a medication therein to retrieve medication information for the medication contained in the container. For example, in one embodiment, the scanner 20 may scan a barcode located on a container having a medication therein. Upon scanning the container with the scanner 20, the medication information about the medication contained in the container is processed by the labeling device 10. For example, the labeling device 10 may refer to a database to process the medication information about the medication contained in the container. In one embodiment, the labeling device 10 may refer to a centralized database to process the medication information about the medication contained in the container. In another embodiment, the labeling device 10 may refer to a local database stored in the labeling device 10 to process the medication information about the medication contained in the container. A user may then select to analyze and/or modify this medication information using the onboard touchscreen interface 22. Potential data fields requiring modification include drug concentration, combinations, and/or other medication identifying information. In one embodiment, the touchscreen interface 22 that is adapted to display the medication information is located on the front portion 54 of housing 14 of labeling device 10.

Referring to FIG. 1, housing 14 of labeling device 10 defines a first compartment 70 adapted to receive a first labeling subsystem 16 and a second compartment 72 adapted to receive a second labeling subsystem 18. In one embodiment, housing 14 includes a divider wall 74 for separating the first compartment 70 and the second compartment 72. The side door 62 may be moved to the open position as shown in FIG. 1 to install the first labeling subsystem 16 and the second labeling subsystem 18 in the labeling device 10. Also, the side door 62 and the top door 66 allow for easy access to the interior of the housing 14 of the labeling device 10 for maintenance work.

Referring to FIGS. 3-14, in one embodiment, a first labeling subsystem 16 is adapted to print a first label 100 including machine readable information 102 (FIG. 2C) and includes a syringe receiving port 104, a syringe clamp assembly 106, and a label print and apply assembly 108.

Figure 2C:
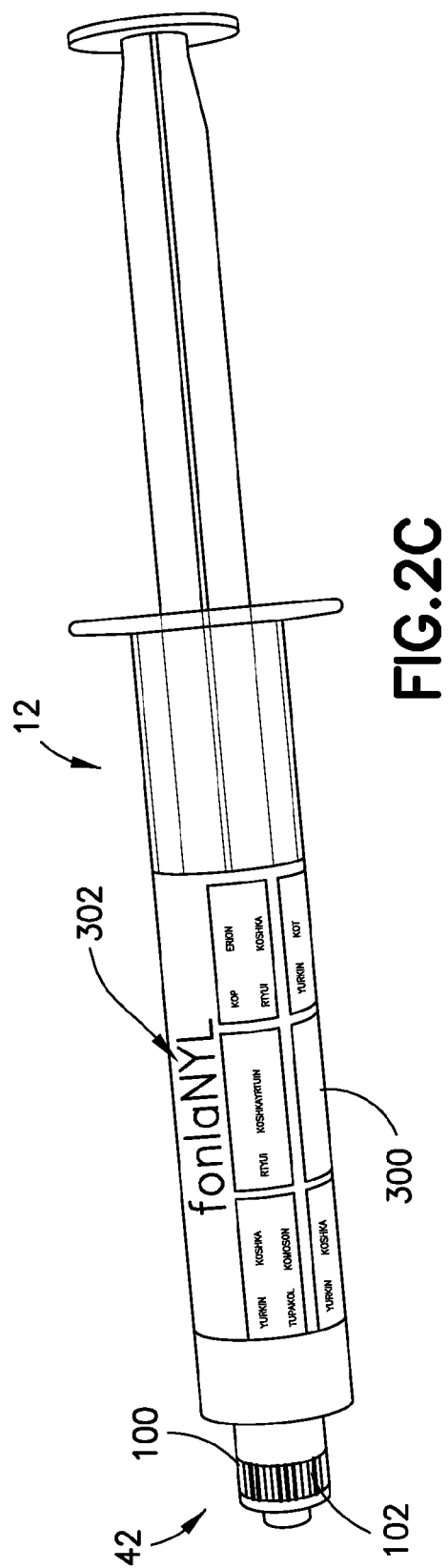
FIG. 2C is a perspective view of a syringe having a first label including machine readable information and a second label having human readable information in accordance with an embodiment of the present invention.

The machine readable information 102 conforms to all applicable standards regarding information contained on a label for a syringe. In one embodiment, the machine readable information 102 is a barcode. For example, the machine readable information 102 may be a unique barcode that is able to record and transmit information related to the syringe and the medication contained therein. Referring to FIG. 2C, the labeling device 10 of the present disclosure provides a first label 100 having machine readable information 102 and a second label 300 having human readable information 302 for a syringe 12 so that a user and/or a machine can easily obtain the desired information regarding the syringe 12 and the contents therein.

Figure 8:
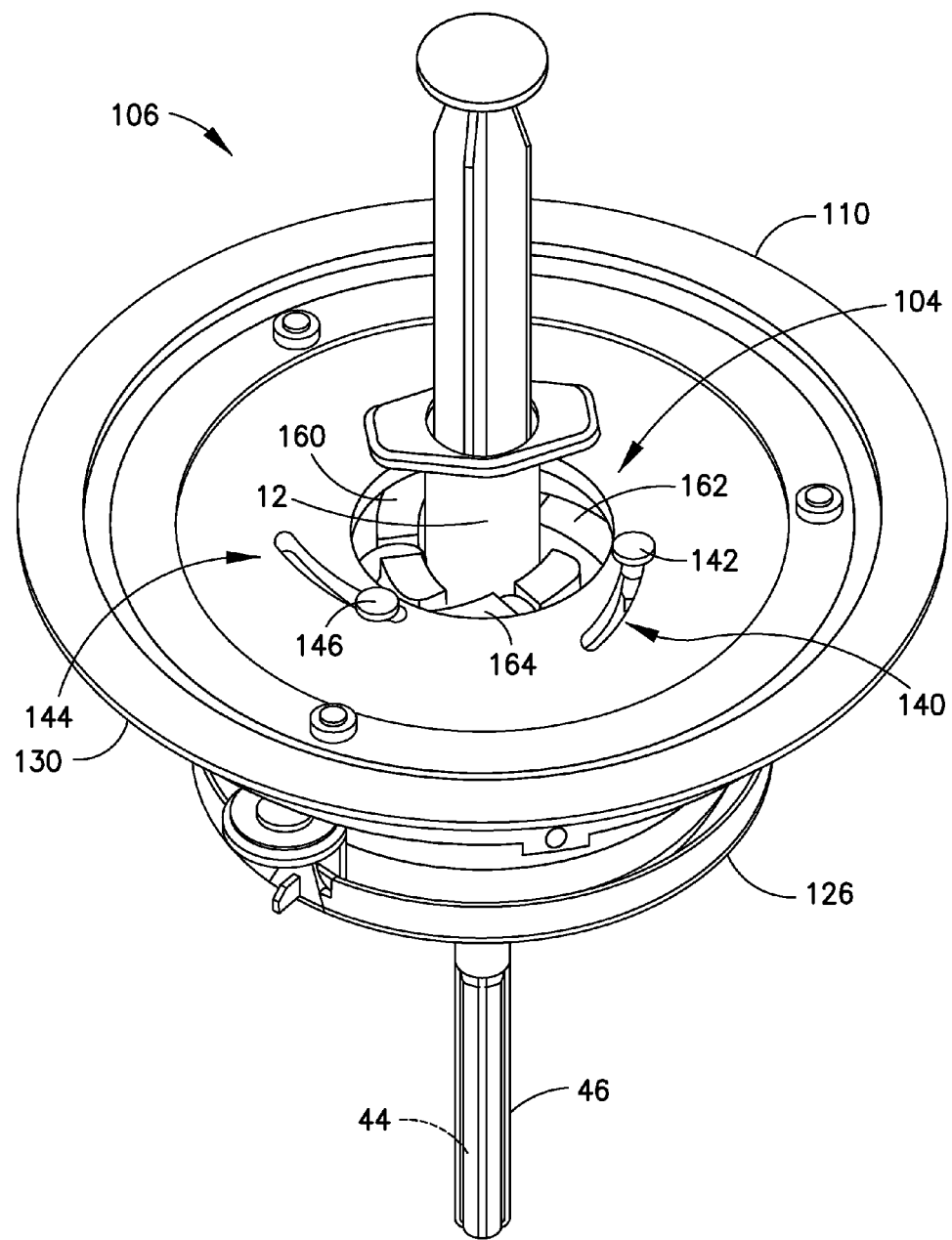
FIG. 8 is a top, perspective view of a syringe clamp assembly with gripping components in a closed position, with a syringe secured within the syringe clamp assembly in accordance with an embodiment of the present invention.
Figure 9:
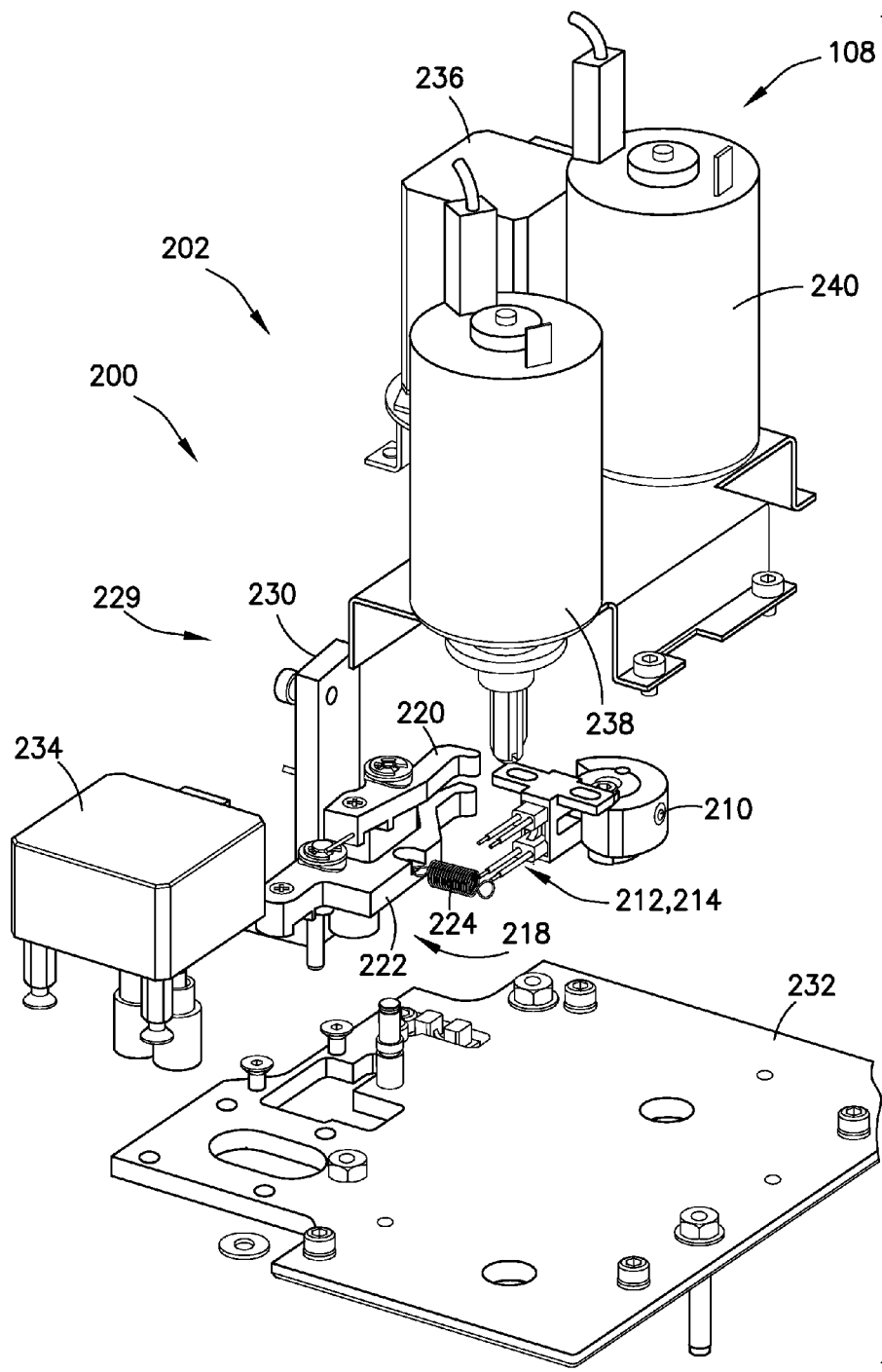
FIG. 9 is an exploded, perspective view of a label print and apply assembly in accordance with an embodiment of the present invention.
Figure 10:
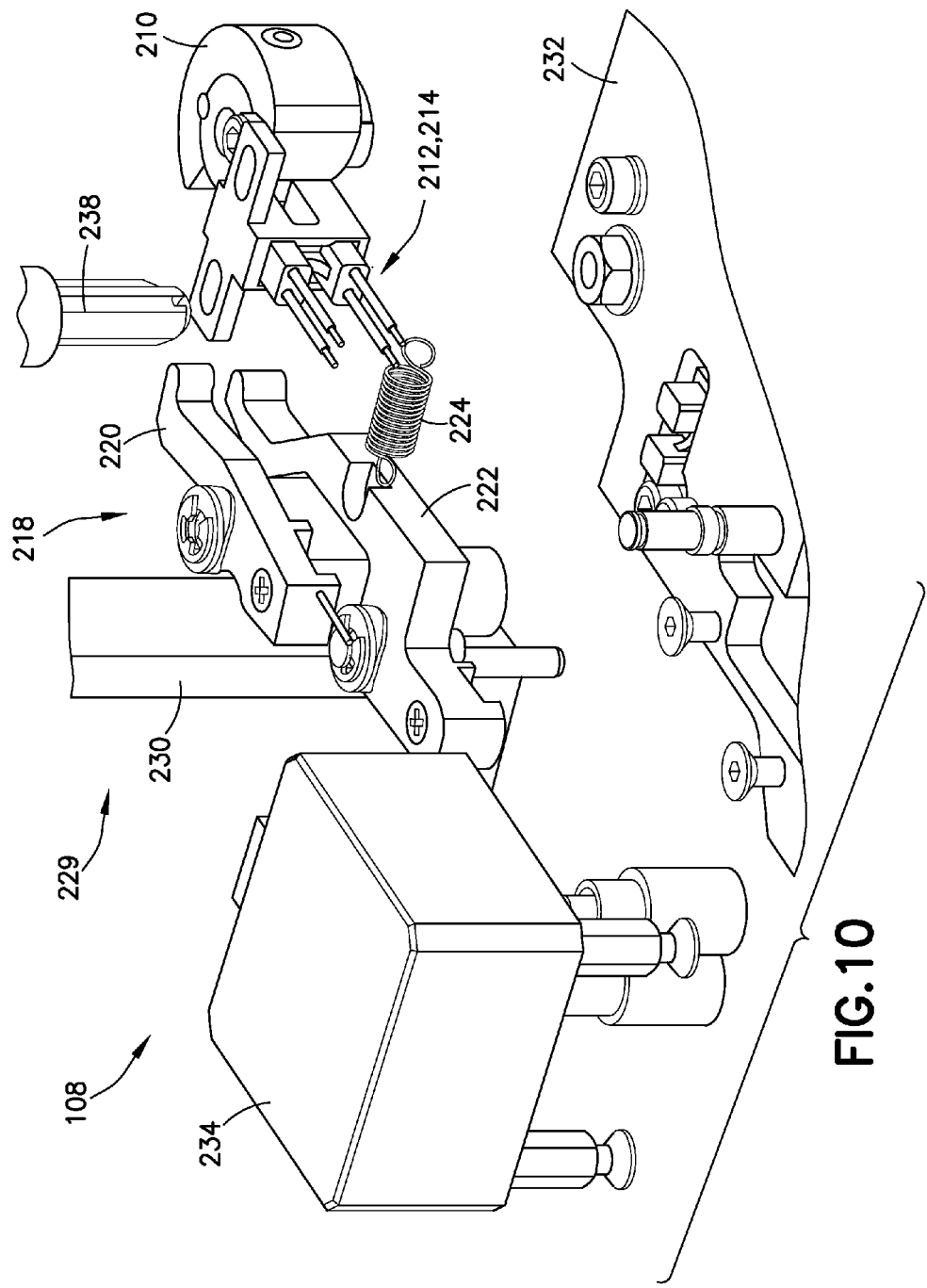
FIG. 10 is a detailed, fragmentary perspective view of a portion of the label print and apply assembly of FIG. 9 in accordance with an embodiment of the present invention.

Referring to FIGS. 1 and 8, the syringe receiving port 104 is adapted to receive a syringe 12 therein for automatic application of a first label 100 to the syringe 12. In one embodiment, the receiving port 104 is located at the top portion 50 of the housing 14 of the labeling device 10. The top door 66 may be moved to the open position as shown in FIG. 1 to insert a syringe 12 within the receiving port 104.

Referring to FIGS. 3-8 and 14, the syringe clamp assembly 106 includes a holding element 110, a drive gear 112, an alignment disc 114, a carrier component 116 having a gear 118, a plurality of gripping components 120, a retaining ring 122, a stability ring 124, and a syringe positioning and alignment component 126. The syringe clamp assembly 106 securely holds the syringe 12 within the syringe receiving port 104 while the label print and apply assembly 108 automatically applies a first label 100 to the luer tip 42 of the syringe 12.

The holding element 110 provides a gripping surface that allows a user to pick up the clamp assembly 106 without having to place their hand within the syringe receiving port 104. In this manner, with the syringe 12 received within the receiving port 104, a user can remove the syringe 12 and/or clamp assembly 106, if needed, without having to place their hand within the syringe receiving port 104 and without having to touch the syringe 12. In one embodiment, the holding element 110 includes a lip portion 130 that extends beyond the periphery of the other components of the clamp assembly 106. In this manner, a user can grasp the holding element 110 at the lip portion 130 to remove the syringe 12 and/or clamp assembly 106. In one embodiment, the outer diameter of the holding element 110 is greater than the outer diameter of the other components of the clamp assembly 106. The holding element 110 includes a central aperture 132 adapted to receive the syringe 12 therethrough.

The drive gear 112 interfaces with a motor and is adapted to open and close the gripping components 120 that are adapted to grip the syringe 12 with the gripping components 120 in the closed position. The motor provides a drive mechanism to rotate the drive gear 112. Additionally, the drive gear 112 is adapted to rotate the syringe 12 during the automatic application of the first label 100 to the syringe 12. In one embodiment, the drive gear 112 includes teeth 134, a first cam slot 136 adapted to receive a first cam post 138, a second cam slot 140 adapted to receive a second cam post 142, a third cam slot 144 adapted to receive a third cam post 146, and a central aperture 148 adapted to receive the syringe 12 therethrough.

The alignment disc 114 is adapted to properly align and maintain the position of the components of the clamp assembly 106. In one embodiment, the alignment disc 114 includes a superior surface 150, an opposing inferior surface 152, a plurality of retaining posts 154 extending from the inferior surface 152, a bearing 156 disposed on each of the retaining posts 154, and a central aperture 158 adapted to receive the syringe 12 therethrough. In one embodiment, the alignment disc 114 includes three retaining posts 154 each having a bearing 156 thereon.

The alignment disc 114 is adapted to allow the components of the clamp assembly 106 to rotate independently of each other so that the gripping components 120 can be opened and closed to grip the syringe 12 with the gripping components 120 in the closed position. Once the gripping components 120 are moved to the closed position to grip the syringe 12, the components of the clamp assembly 106 are then capable of rotating together to rotate the syringe 12 during the automatic application of the first label 100 to the syringe 12. In one embodiment, the syringe 12 is rotated during the automatic application of the first label 100 to the syringe 12 while the first label 100 remains in a stationary position.

The carrier component 116 includes a gear 118 extending around the periphery of the carrier component 116, protruding walls 170 each defining a rod aperture 172, and a central aperture 174 adapted to receive the syringe 12 therethrough. The carrier component 116 provides a carrier that the other components of the clamp assembly 106 can be secured to. In one embodiment, the carrier component 116 is formed of steel, although other materials of similar strength may be used. The components of the clamp assembly 106 can be secured to the carrier component 116 using methods known in the art. In one embodiment, any suitable fastener can be used to secure the components of the clamp assembly 106 to the carrier component 116 such as a bolt or a threaded fastener. The carrier component 116 includes protruding walls 170 that define rod apertures 172 therethrough. The protruding walls 170 extend from the carrier component 116 inward to the central aperture 174. In one embodiment, the carrier component 116 includes three protruding walls 170 each defining a rod aperture 172. The carrier component 116 also includes the central aperture 174 adapted to receive the syringe 12 therethrough.

Figure 4:
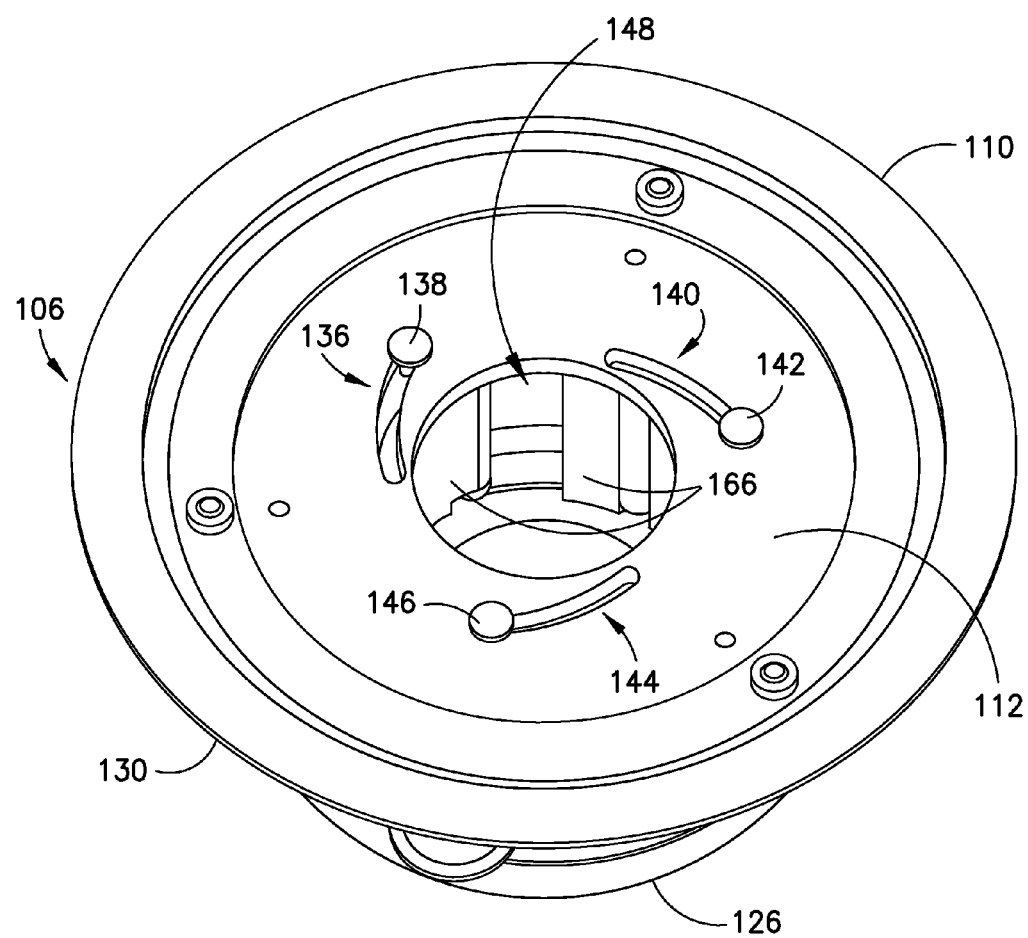
FIG. 4 is an assembled, perspective view of a syringe clamp assembly with gripping components in an open position in accordance with an embodiment of the present invention.
Figure 5:
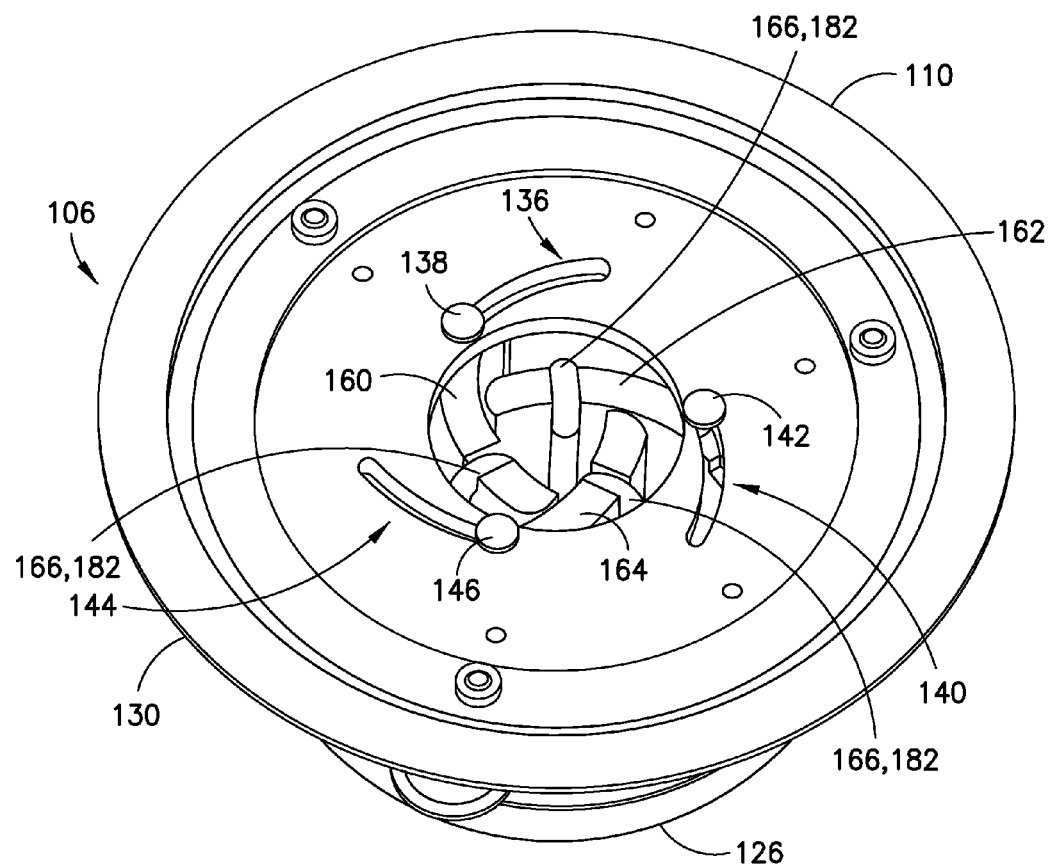
FIG. 5 is an assembled, perspective view of a syringe clamp assembly with gripping components in a closed position in accordance with an embodiment of the present invention.
Figure 6A:
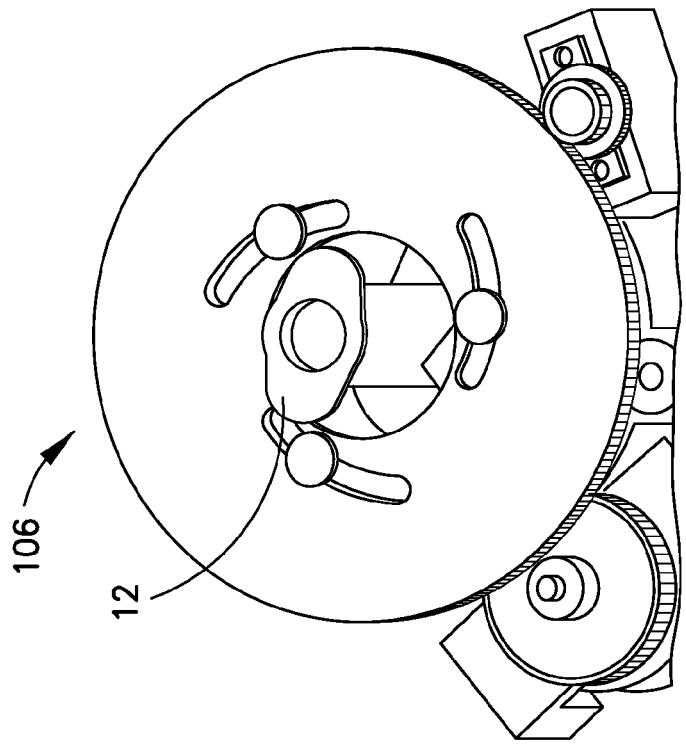
FIG. 6A is a top, perspective view of a syringe clamp assembly with gripping components in an open position, with a syringe positioned within the syringe clamp assembly in accordance with an embodiment of the present invention.
Figure 6B:
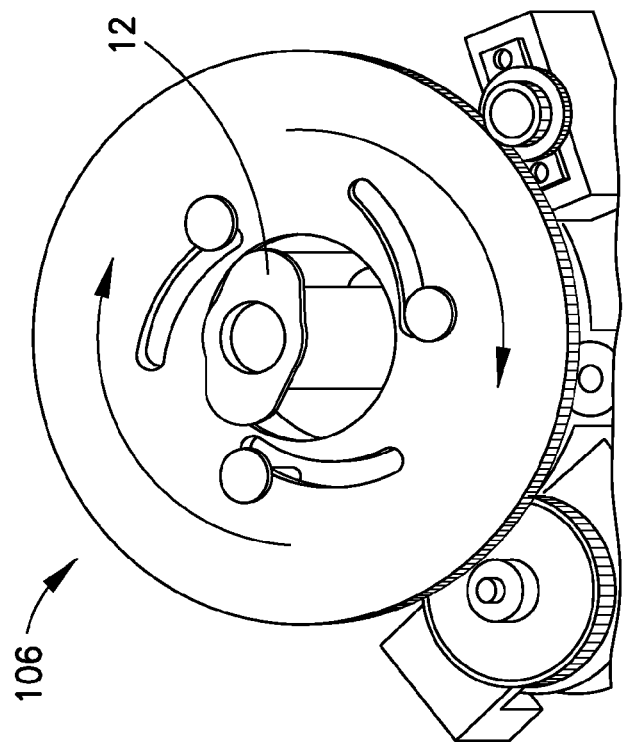
FIG. 6B is a top, perspective view of a syringe clamp assembly with gripping components in a partially closed position, with a syringe positioned within the syringe clamp assembly in accordance with an embodiment of the present invention.
Figure 7:
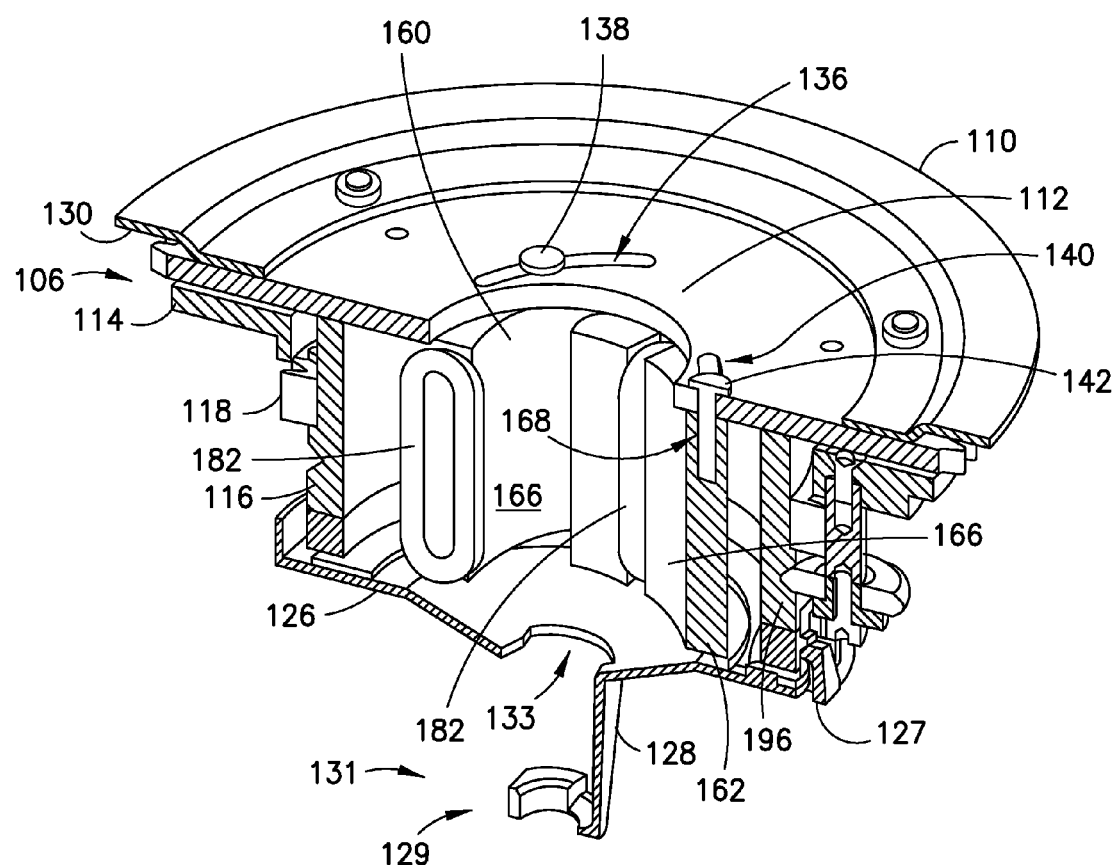
FIG. 7 is a cross-sectional view of a syringe clamp assembly in accordance with an embodiment of the present invention.

The gripping components 120 are movable between an open position (FIG. 4) and a closed position (FIGS. 5 and 8). With the gripping components 120 in the closed position, the gripping components 120 contact and grip the syringe 12 to secure the syringe 12 within the syringe receiving port 104 of the first labeling subsystem 16 of the labeling device 10 as shown in FIG. 8. Additionally, as the gripping components 120 move to the closed position to contact and grip the syringe 12, the gripping components 120 also center the syringe 12 to the proper orientation within the clamp assembly 106 for the automatic application of the first label 100 to the syringe 12. In one embodiment, the gripping component 120 includes a first jaw 160, a second jaw 162, and a third jaw 164 that each include a gripping surface 166, a cam post receiving aperture 168, and a rod receiving aperture 180. In one embodiment, the first jaw 160, the second jaw 162, and the third jaw 164 each include a grip element 182 to contact and grip the syringe 12 to further secure the syringe 12 within the syringe receiving port 104 of the first labeling subsystem 16 of the labeling device 10 as shown in FIG. 8.

In one embodiment, the gripping components 120 are adapted to securely hold any size of syringe 12 within the syringe receiving port 104 while the label print and apply assembly 108 automatically applies a first label 100 to the luer tip 42 of the syringe 12. In other embodiments, the gripping components 120 are adapted to securely hold a syringe 12 having any size from 1 mL to 60 mL within the syringe receiving port 104 while the label print and apply assembly 108 automatically applies a first label 100 to the luer tip 42 of the syringe 12.

The retaining ring 122 includes a superior surface 186, an opposing inferior surface 188, a plurality of posts 190 extending from the inferior surface 188 and each defining a rod receiving aperture 192, and a central aperture 194 adapted to receive the syringe 12 therethrough.

Figure 3:
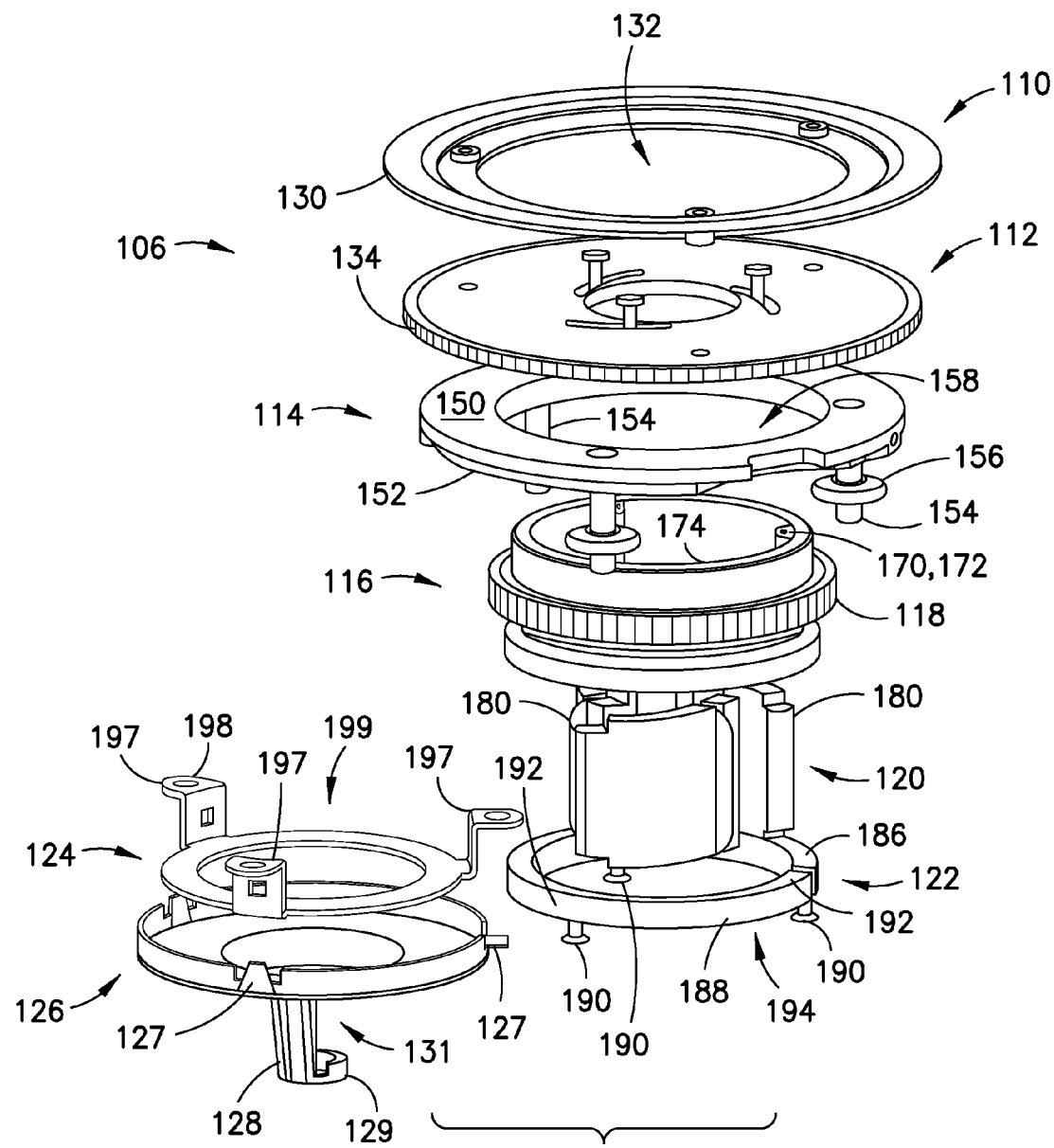
FIG. 3 is an exploded, perspective view of a syringe clamp assembly in accordance with an embodiment of the present invention.

Referring to FIGS. 3-8, the assembly of the syringe clamp assembly 106 of first labeling subsystem 16 of labeling device 10 will now be described. The gripping components 120 are movable between an open position (FIG. 4) and a closed position (FIGS. 5 and 8). The gripping components 120 are pivotably connected to the carrier component 116 and retaining ring 122 so that the gripping components 120 are movable between the open position and the closed position. In one embodiment, connecting rods 196 are used to pivotably connect the gripping components 120 to the carrier component 116 and retaining ring 122. Referring to FIG. 3, the respective rod apertures 172 of the carrier component 116 are aligned with the rod receiving apertures 180 of the respective jaws 160, 162, 164 and the respective rod receiving apertures 192 of the retaining ring 122. In this manner, connecting rods 196 can be positioned through the rod apertures 172 of the carrier component 116 and through the rod receiving apertures 180 of the respective jaws 160, 162, 164 and through the respective rod receiving apertures 192 of the retaining ring 122 to pivotably connect the jaws 160, 162, 164 to the carrier component 116 and retaining ring 122. In this manner, the jaws 160, 162, 164 are pivotably connected to the carrier component 116 and retaining ring 122 so that the jaws 160, 162, 164 are movable between the open position and the closed position.

Movement of the jaws 160, 162, 164 between the open position and the closed position is controlled by a movable cam connection between the jaws 160, 162, 164 and the drive gear 112. In one embodiment, the respective cam slots 136, 140, 144 of the drive gear 112 are aligned with the cam post receiving apertures 168 of the respective jaws 160, 162, 164. In this manner, cam posts 138, 142, 146 can be positioned through the respective cam slots 136, 140, 144 of the drive gear 112 and through the cam post receiving apertures 168 of the respective jaws 160, 162, 164 to movably connect the jaws 160, 162, 164 to the drive gear 112. In this manner, the drive gear 112 controls movement of the jaws 160, 162, 164 between the open position and the closed position.

In one embodiment, the first cam slot 136, the second cam slot 140, and the third cam slot 144 are positioned off-center so that rotation of the drive gear 112 with the carrier component 116 in a stationary position moves the jaws 160, 162, 164 between the open position and the closed position via the sliding movement of the cam posts 138, 142, 146 within the off-center cam slots 136, 140, 144.

Referring to FIG. 3, in one embodiment, the first labeling subsystem 16 includes a stability ring 124 and a syringe positioning and alignment component 126. The stability ring 124 includes bent tabs 197 each defining an aperture 198 and a central aperture 199 adapted to receive the syringe 12 therethrough. In one embodiment, the stability ring 124 includes three bent tabs 197. The stability ring 124 is connected to the alignment disc 114. For example, in one embodiment, the retaining posts 154 of the alignment disc 114 are connected to a respective bent tab 197 through apertures 198. In one embodiment, the retaining posts 154 are threadingly connected to the respective bent tabs 197 of the stability ring 124. In this manner, the stability ring 124 provides stability to the components of the first labeling subsystem 16.

The syringe alignment component 126 is removably connected to the stability ring 124. The syringe alignment component 126 includes flexible arms 127, a wall 128 that extends downwardly from the syringe alignment component 126, a luer tip receiving portion 129, an alignment area 131, and a central aperture 133 adapted to receive the luer tip 42 of the syringe 12 therethrough. In one embodiment, the syringe alignment component 126 is removably connected to the stability ring 124 via a snap fit engagement. For example, the flexible arms 127 can be used to snap fit the syringe alignment component 126 to the stability ring 124.

The flexible arms 127 can be deformed to an open position so that the syringe alignment component 126 can be removed from the stability ring 124. With the syringe 12 positioned within the syringe receiving port 104, the luer tip 42 of the syringe 12 extends beyond the central aperture 133 to the luer tip receiving portion 129 within the alignment area 131. In this manner, the luer tip 42 of the syringe 12 is properly positioned within the first labeling subsystem 16 so that an optical syringe alignment unit 250 (FIG. 12) can determine the precise position of the luer tip 42 of the syringe 12 for automatic application of the first label 100 to the luer tip 42 of the syringe 12 as discussed below.

A syringe clamp assembly of the first labeling subsystem 16 may include other embodiments to securely hold a syringe 12 within the syringe receiving port 104 while the label print and apply assembly 108 automatically applies a first label 100 to the luer tip 42 of the syringe 12.

Figure 22:
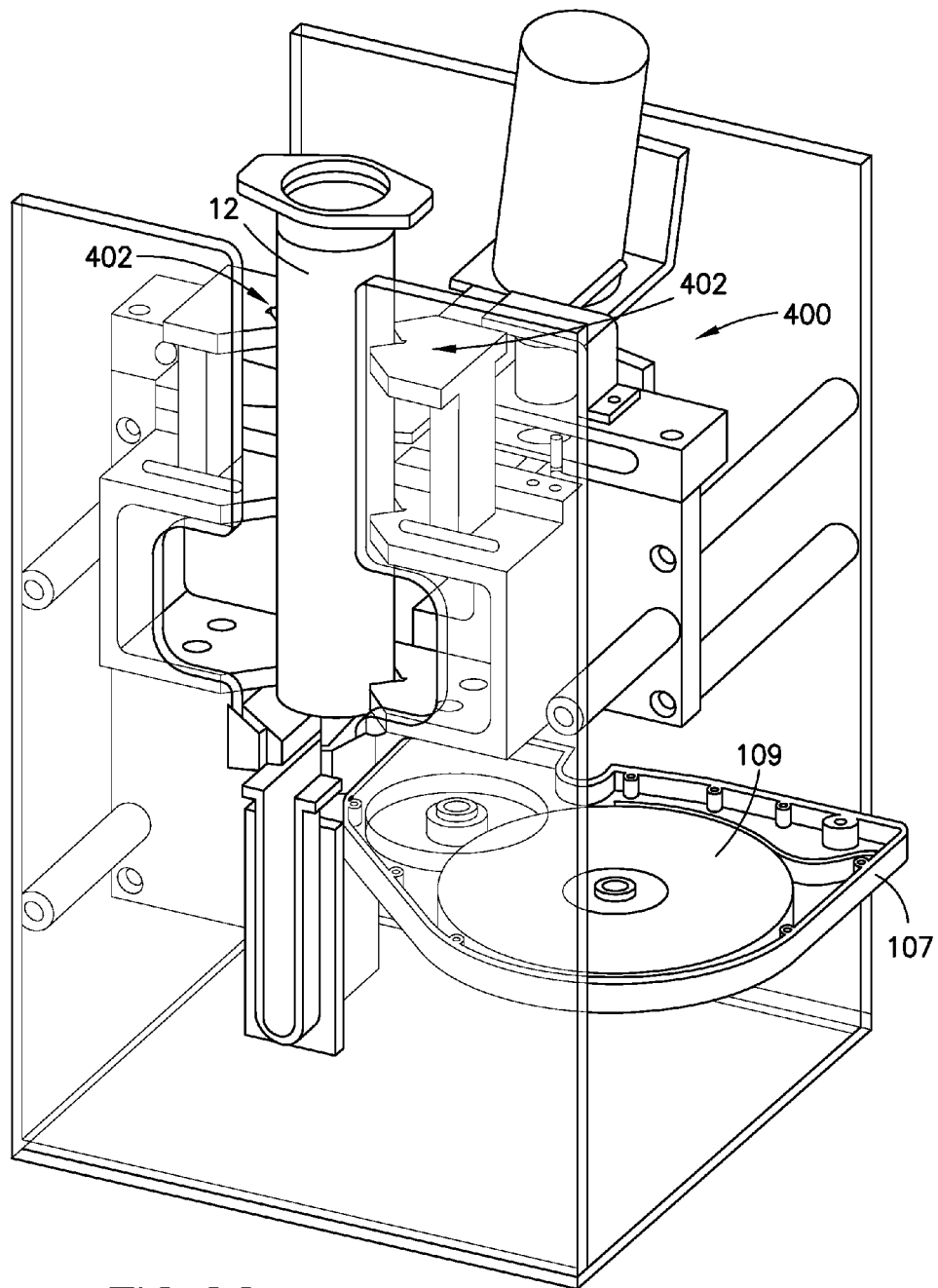
FIG. 22 is a perspective view of a first labeling subsystem, with a syringe secured within the first labeling subsystem for the automatic application of a first label to the syringe in accordance with another embodiment of the present invention.

Referring to FIG. 22, in another embodiment, a syringe clamp assembly 400 includes an opposing V-shaped clamp assembly. In this embodiment, a syringe 12 is placed between two spring loaded V-shaped jaws 402. Once the syringe 12 is properly placed within the jaws 402, an electromagnet would activate, locking the jaws 402 in a closed position to securely hold a syringe 12 within the syringe clamp assembly 400 while the label print and apply assembly 108 automatically applies a first label 100 to the luer tip 42 of the syringe 12. A roller would then make contact with the syringe 12, rotating it about its axis. The roller would be orientated at an angle to the rotation, forcing the syringe 12 to move axially until the luer tip 42 of the syringe 12 rested against a reference surface. Once the luer tip 42 of the syringe 12 was in position, the label print and apply assembly 108 would automatically apply a first label 100 to the luer tip 42 of the rotating syringe 12.

Figure 23:
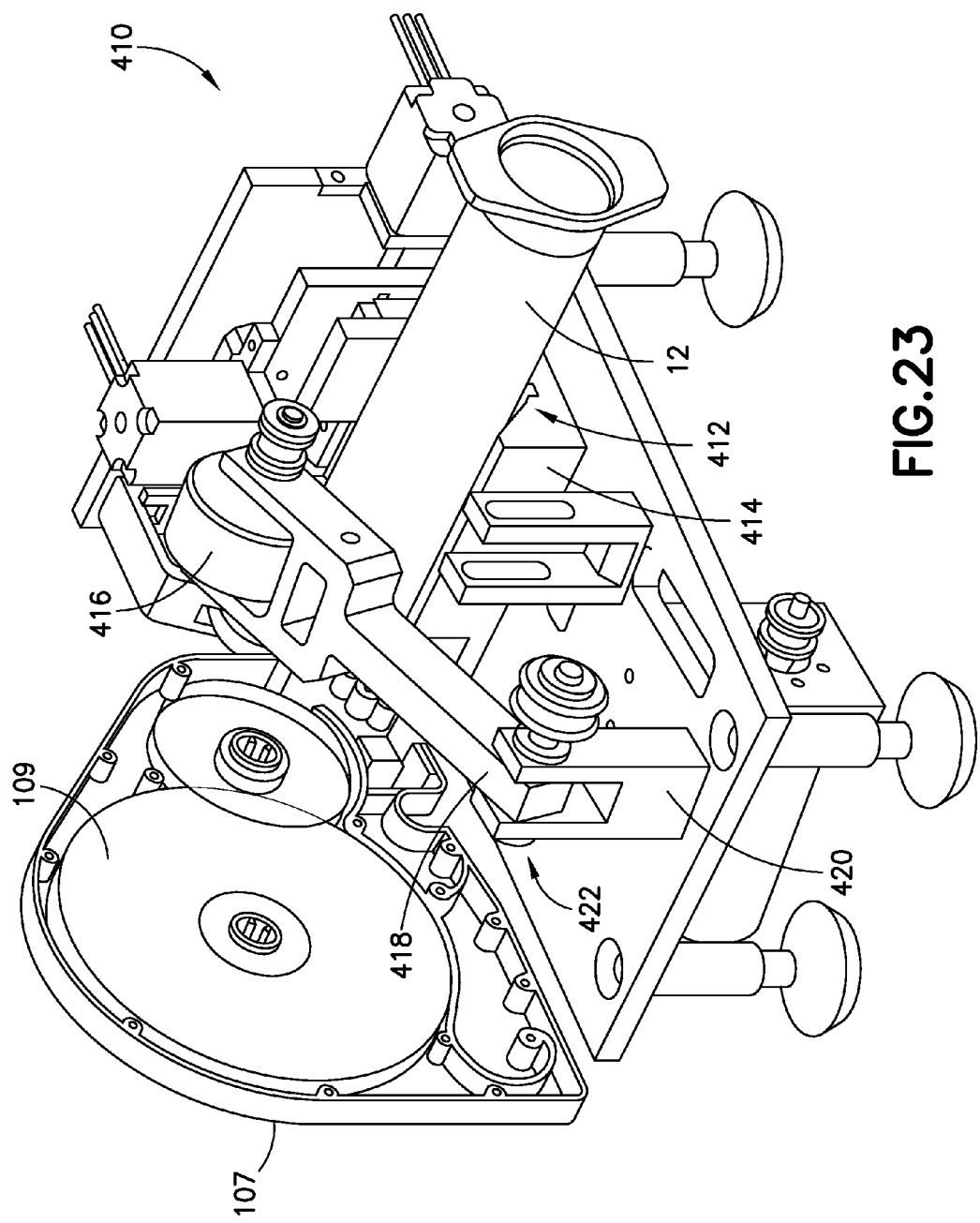
FIG. 23 is a perspective view of a first labeling subsystem, with a syringe secured within the first labeling subsystem for the automatic application of a first label to the syringe in accordance with another embodiment of the present invention.

Referring to FIG. 23, in another embodiment, a syringe clamp assembly 410 includes an oblique roller clamp assembly. In this embodiment, a syringe 12 is placed in a V-shaped groove 412 of a syringe holding component 414 and a roller 416 rotatably connected to an arm 418 would be lowered until it contacted the syringe 12 and made the syringe 12 rotate about its axis. In this embodiment, the arm 418 is movably connected to a base portion 420 via a pin connection 422 at the base portion 420. The roller 416 would be orientated at an angle to the rotation, forcing the syringe 12 to move axially until the luer tip 42 of the syringe 12 rested against a reference surface. Simultaneously, the entire mechanism would move in a manner such that the outer radius of the luer tip 42 of the syringe 12 would be tangent to the tip of the label application mechanism. Once the luer tip 42 of the syringe 12 was in position, the label print and apply assembly 108 would automatically apply a first label 100 to the luer tip 42 of the rotating syringe 12.

In another embodiment, a syringe clamp assembly of the present disclosure includes a cap clamp assembly. In this embodiment, the cap clamp assembly utilizes a collet to grab a syringe cap and pull it against a datum surface for axial registration. The cap clamp assembly would also rotate the syringe 12 similar to the opposing V-shaped clamp assembly and the oblique roller clamp assembly for automatic application of a first label 100 to the luer tip 42 of the rotating syringe 12.

Referring to FIGS. 9-14, the label print and apply assembly 108 includes a first label print assembly 200 and a label apply assembly 202. The first label print assembly 200 of the label print and apply assembly 108 is activated during the printing of a first label 100 and the label apply assembly 202 of the label print and apply assembly 108 is activated during the automatic application of the first label 100 to a syringe 12. The label print and apply assembly 108 includes the first label print assembly 200, the label apply assembly 202, a sensor component 210, a print and apply state controller 218, a first printer device 229 having a label printer head 230, a mounting plate 232, a first motor 234, a second motor 236, a third motor 238, a fourth motor 240, an optical syringe alignment unit 250, and a pinch roller mechanism 260. In one embodiment, the first printer device 229 allows for thermal printing of the first label 100 for the luer tip 42 of the syringe 12.

The label print and apply assembly 108 includes a sensor component 210 having a sensor arm 212 that is used as a photo interrupter and a cam element 214. The sensor component 210 is rotatable between a first position and a second position. In one embodiment, the sensor component 210 interfaces with a motor. The motor provides a drive mechanism to rotate the sensor component 210 between the first position and the second position. In one embodiment, with the sensor component 210 rotated to the second position, the sensor arm 212 breaks an optical beam. In this manner, the position of the sensor component 210 is determined and the label print and apply assembly 108 can be activated in accordance with the position of the sensor component 210. In one embodiment, rotation of the sensor component 210 moves the cam element 214 between a first position and a second position.

The label print and apply assembly 108 includes a print and apply state controller 218 that activates the first label print assembly 200 to print a first label 100 and activates the label apply assembly 202 to automatically apply the first label 100 to a syringe 12. In one embodiment, the print and apply state controller 218 includes a first flipper arm 220 and a second flipper arm 222 which are spring loaded. In one embodiment, the first flipper arm 220 and the second flipper arm 222 are spring loaded by spring 224. The first flipper arm 220 and the second flipper arm 222 are movable between a first position, in which the first label print assembly 200 is activated to print a first label 100, and a second position, in which the label apply assembly 202 is activated to automatically apply the first label 100 to a syringe 12. In one embodiment, the first flipper arm 220 and the second flipper arm 222 interface with the cam element 214. Thus, rotation of the cam element 214 between a first position and a second position moves the first flipper arm 220 and the second flipper arm 222 between the first position and the second position.

Figure 13:
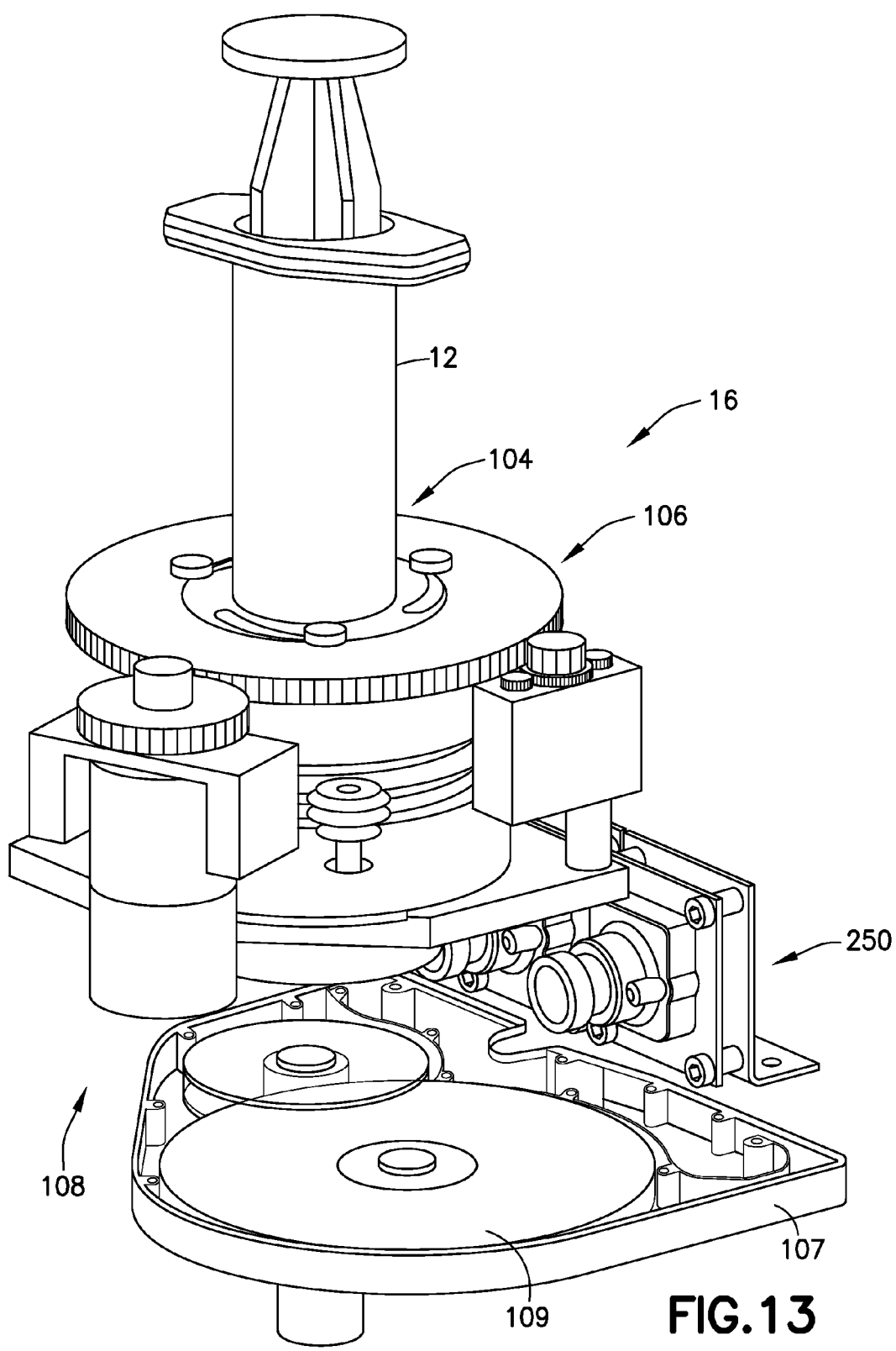
FIG. 13 is a perspective view of a first labeling subsystem, with a syringe secured within the first labeling subsystem for the automatic application of a first label to the syringe in accordance with an embodiment of the present invention.

The first flipper arm 220 and the second flipper arm 222 control pressure rollers on the label path that allow the first label 100 to be printed via the first label print assembly 200 or applied via the label apply assembly 202. For example, in one embodiment, with the first flipper arm 220 and the second flipper arm 222 in a first position, the flipper arms 220, 222 control a first pressure roller to force a cartridge, spool, or reel containing a label up against a label printer head 230 and feeds the label through the label printer head 230 for the printing of machine readable information on a first label 100. Referring to FIG. 13, in one embodiment, label material 109 for the printing of machine readable information 102 thereon to create first labels 100 may be contained in a cartridge 107 that allows for simple loading. In one embodiment, the cartridge 107 includes a removal device adapted to automatically remove the backing material of the first label 100. In one embodiment, the removal device comprises a knife edge portion to contact and remove the backing material of the first label 100.

After printing, the first flipper arm 220 and the second flipper arm 222 can be rotated to a second position so that the first pressure roller is disconnected from the label path and a second pressure roller clamps down and feeds the first label 100 containing machine readable information forward for the peeling off of the first label 100 from a backing material for the automatic application of the first label 100 to a syringe 12.

The label print and apply assembly 108 includes a mounting plate 232 for controlling the position and securing the components of the label print and apply assembly 108. In one embodiment, the components of the label print and apply assembly 108 can be secured to the mounting plate 232 using fasteners and methods known in the art.

The label print and apply assembly 108 includes a first motor 234, a second motor 236, a third motor 238, and a fourth motor 240 to operate the label print and apply assembly 108. In one embodiment, the first motor 234 and the second motor 236 are stepper motors which allow for the indexing and controlling of the position of the first label 100 so that the printing of the machine readable information onto the first label 100 is printed and applied properly.

In one embodiment, the third motor 238 and the fourth motor 240 provide tension to the reel of labels so that the labels are held tightly and do not wrinkle, tangle, and/or crease. In this manner, the printing of the machine readable information onto the first label 100 is printed and applied properly to the first label 100.

Figure 12:
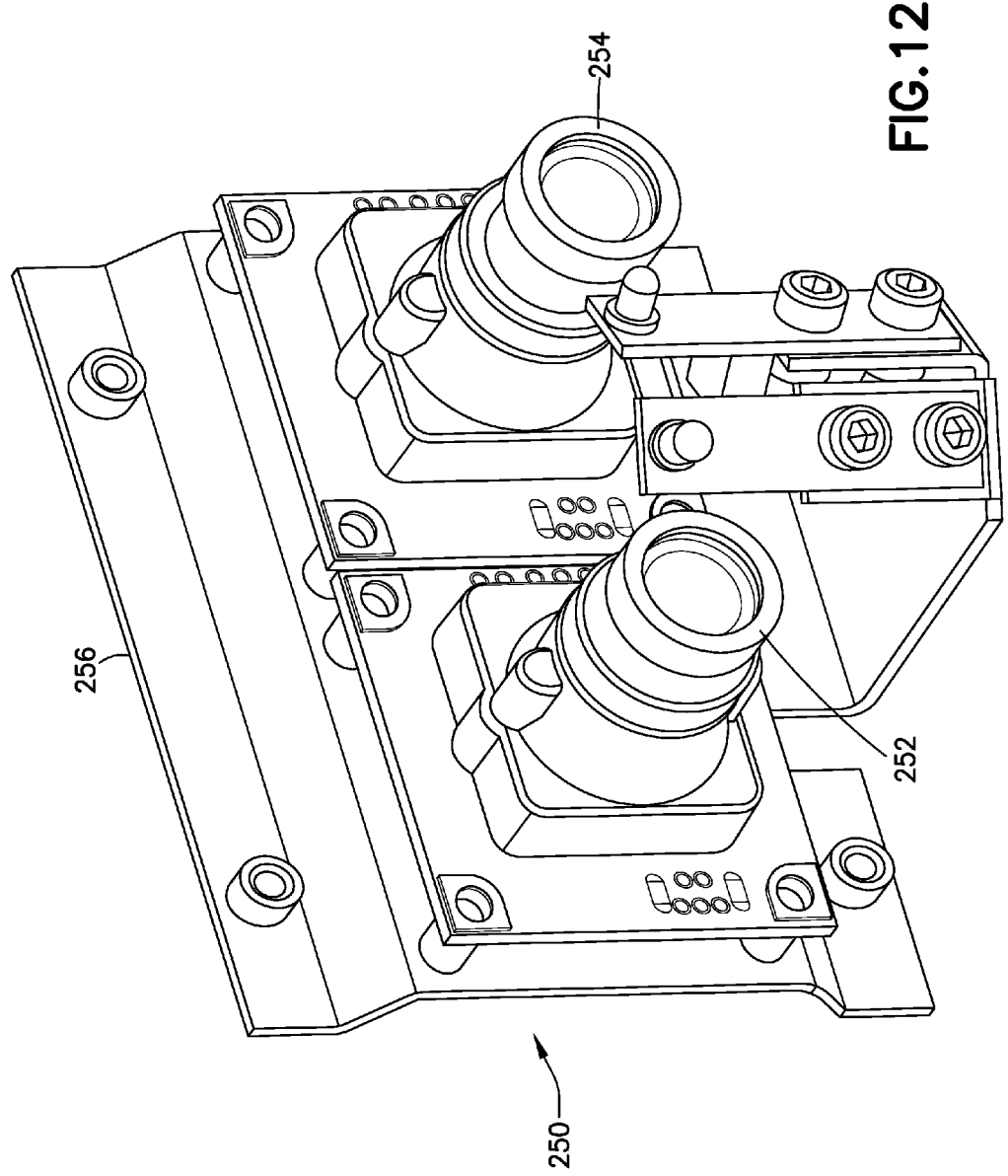
FIG. 12 is a perspective view of an optical syringe alignment unit in accordance with an embodiment of the present invention.

Referring to FIGS. 12 and 13, the label print and apply assembly 108 includes an optical syringe alignment unit 250 having a first camera 252, a second camera 254, and a mounting bracket 256. The optical syringe alignment unit 250 is positioned so that the first camera 252 and the second camera 254 are positioned adjacent the alignment area 131 of the syringe positioning and alignment component 126 as shown in FIG. 13. In this manner, with the syringe 12 positioned within the syringe receiving port 104 and the luer tip 42 of the syringe 12 extending into the alignment area 131 of the syringe positioning and alignment component 126, the first camera 252 and the second camera 254 are able to locate the luer tip 42 of the syringe 12. For example, the first camera 252 is able to locate the precise position of the syringe 12 and luer tip 42 for automatic application of the first label 100 to the luer tip 42 of the syringe 12. In one embodiment, the second camera 254 is able to inspect the machine readable information 102 on the first label 100 as the first label 100 is automatically being applied to the luer tip 42 of the syringe 12. In another embodiment, the second camera 254 is able to inspect the machine readable information 102 on the first label 100 after the first label 100 is automatically applied to the luer tip 42 of the syringe 12.

The mounting bracket 256 is adapted to connect the optical syringe alignment unit 250 so that the first camera 252 and the second camera 254 are positioned adjacent the alignment area 131 of the syringe positioning and alignment component 126. In one embodiment, the mounting bracket 256 is connectable to an interior wall portion of the housing 14 of the labeling device 10.

Figure 11:
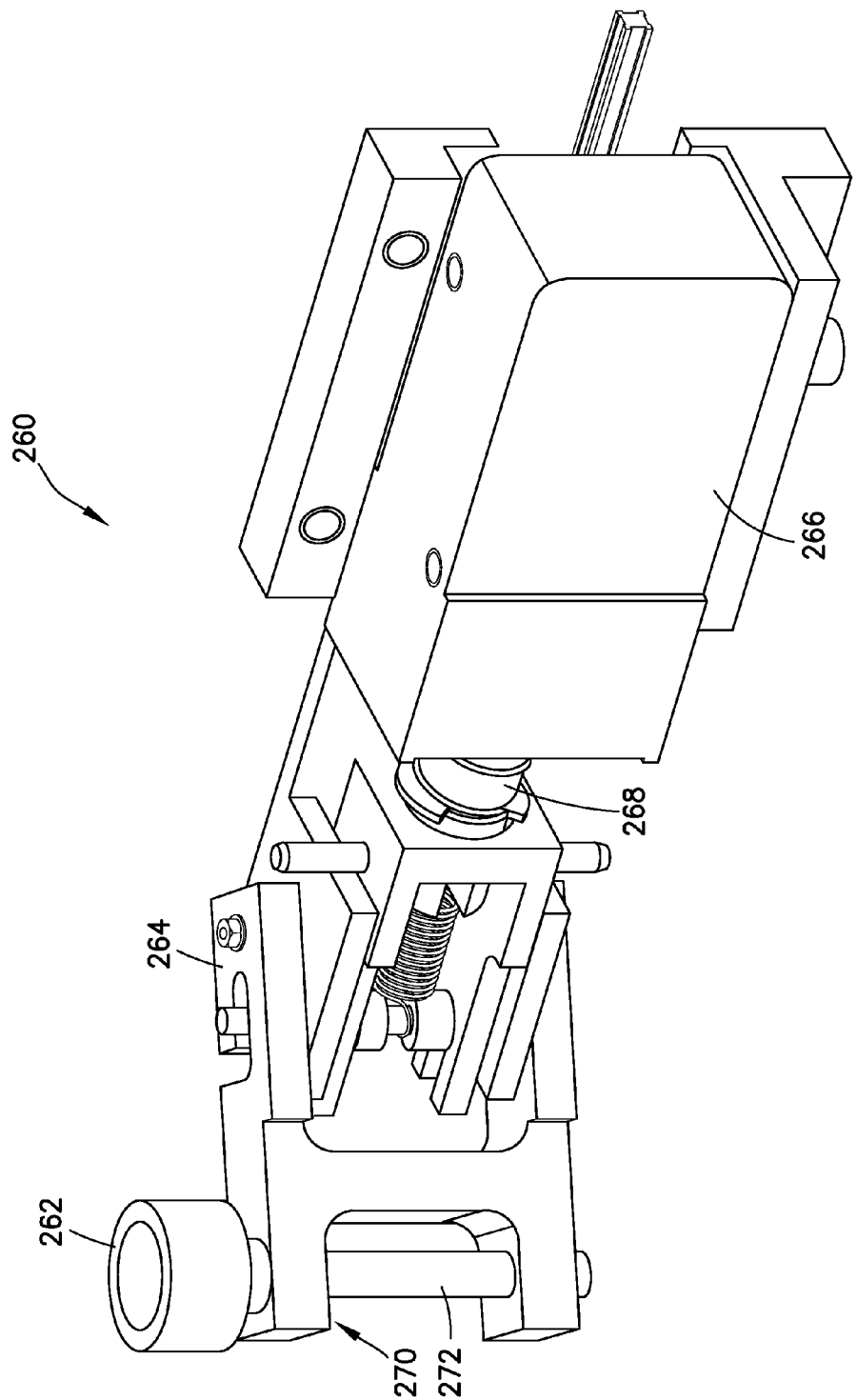
FIG. 11 is a perspective view of a pinch roller mechanism in accordance with an embodiment of the present invention.
Figure 14:
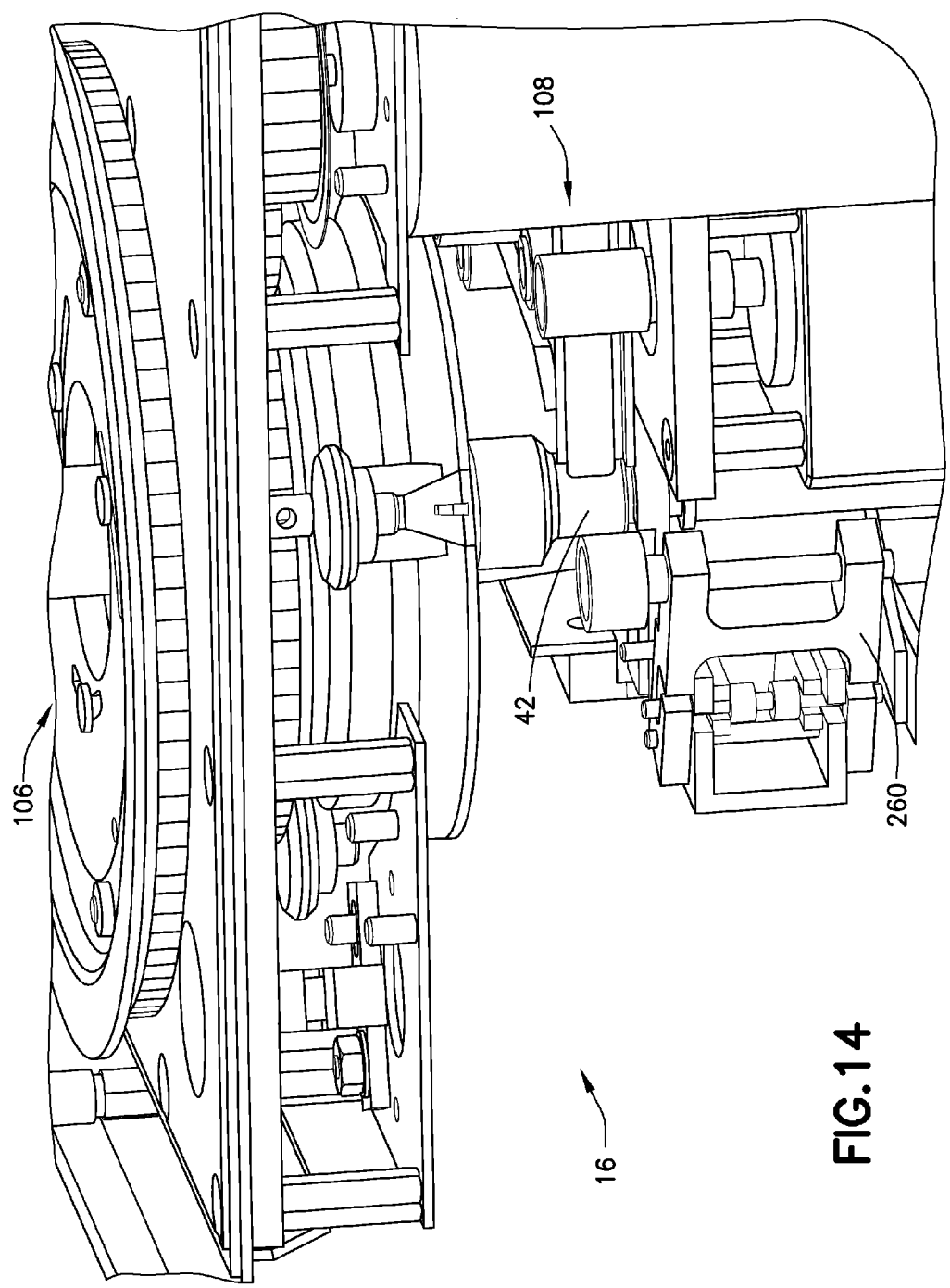
FIG. 14 is a detailed, fragmentary perspective view of a portion of a first labeling subsystem, with a syringe secured within the first labeling subsystem for the automatic application of a first label to the syringe in accordance with an embodiment of the present invention.

Referring to FIGS. 11 and 14, the label print and apply assembly 108 includes a pinch roller mechanism 260 for exerting a force on the first label 100 as the first label 100 is automatically being applied to the luer tip 42 of the syringe 12 to ensure that the first label 100 is securely applied to the syringe 12.

The pinch roller mechanism 260 includes a roller contact portion 262, a pivotable frame member 264, and a solenoid 266 including an actuation member 268. The solenoid 266 is adapted to move the actuation member 268 forward and backward. The pivotable frame member 264 is movably connected to the actuation member 268 of the solenoid 266. Movement of the actuation member 268 of the solenoid 266 forward causes the frame member 264 to pivot such that the roller contact portion 262 can be positioned to contact a portion of the first label 100 as the first label 100 is automatically being applied to the luer tip 42 of the syringe 12 to ensure that the first label 100 is securely applied to the syringe 12. In one embodiment, the frame member 264 includes a receiving aperture 270 and the roller contact portion 262 includes a rod 272 that is received within the receiving aperture 270 so that the roller contact portion 262 is rotatably connected to the frame member 264.

Figure 15:
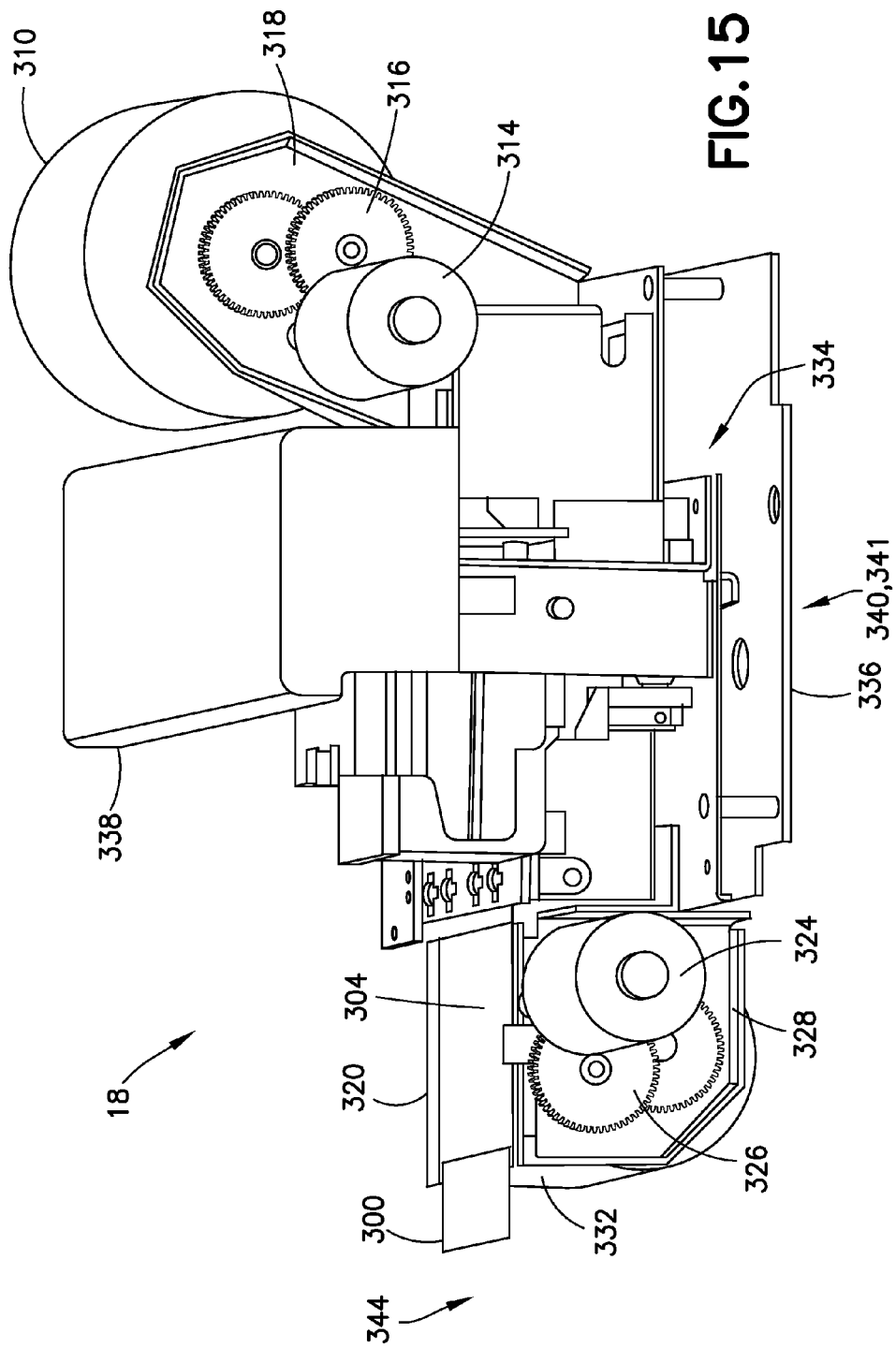
FIG. 15 is a perspective view of a second labeling subsystem in accordance with an embodiment of the present invention.
Figure 16:
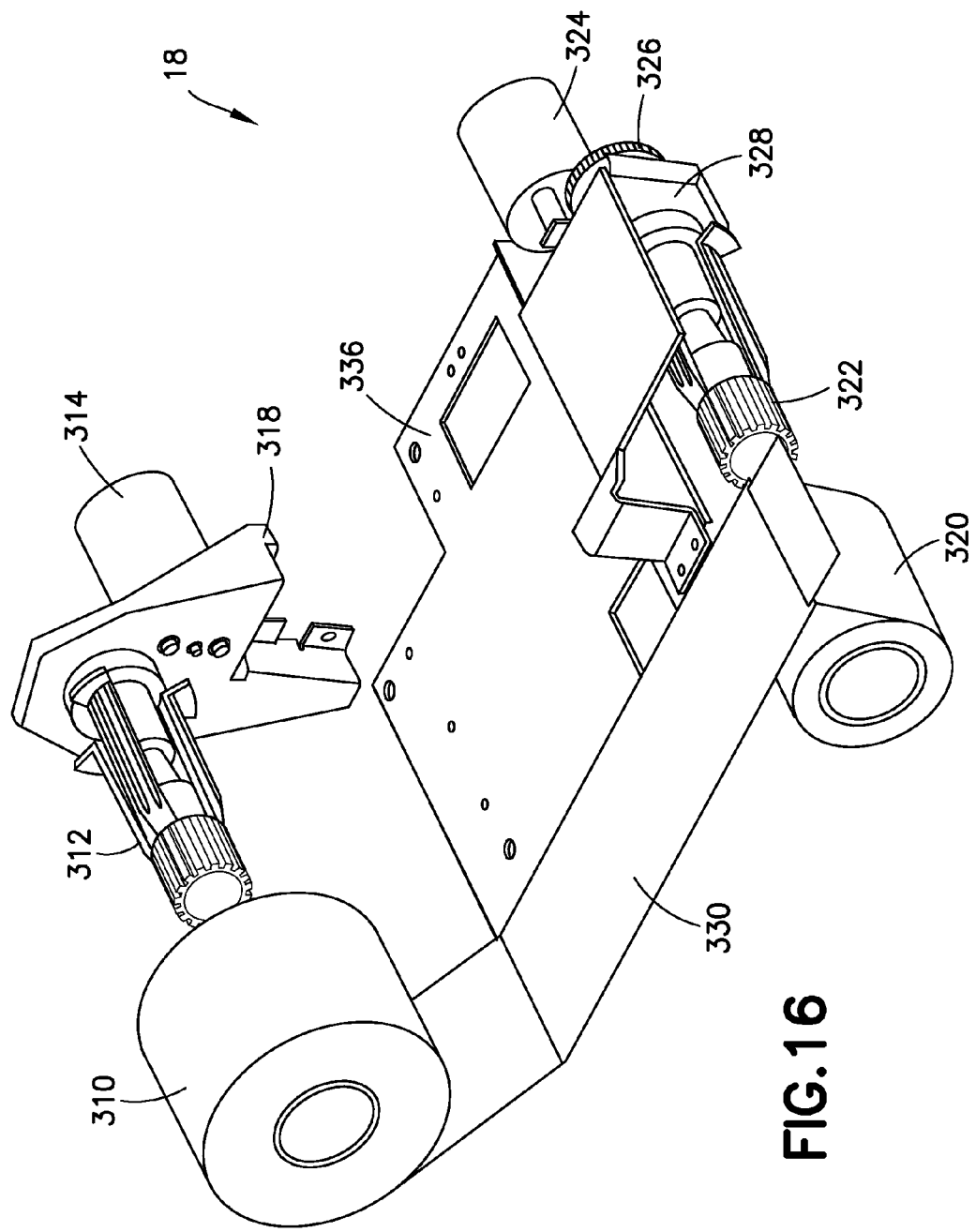
FIG. 16 is an exploded, perspective view of a second labeling subsystem in accordance with an embodiment of the present invention.

Referring to FIGS. 15-21, in one embodiment, a tensioning control device or second labeling subsystem 18 is adapted to print a second label 300 including human readable information 302 and includes a first or supply label roll 310, a first label actuator 312, a first motor 314, a first gear system 316, a first mounting portion 318, a second or windup label roll 320, a second label actuator 322, a second motor 324, a second gear system 326, a second mounting portion 328, a substrate or movable label portion 330 between the first label roll 310 and the second label roll 320, a removal device 332 adapted to automatically remove a backing material 304 from the second label 300, an actuator or index control system 334, a mounting plate 336, a cover 338, and a second printer device 340 having a label printer head 341. Referring to FIGS. 1 and 15, the cover 338 provides for protection of the components of the second labeling subsystem 18.

In one embodiment, the second labeling subsystem 18 includes components that allow the second labeling subsystem 18 to automatically apply a second label 300 to a portion of the syringe 12. In one embodiment, the second labeling subsystem 18 automatically applies a second label 300 to a portion of the syringe 12 simultaneously with the first labeling subsystem 16 automatically applying a first label 100 to a portion of the syringe 12.

The human readable information 302 may be in full color and conforms to all applicable standards regarding layout and information contained on a label for a syringe. In this manner, the labeling device 10 provides a first label 100 having machine readable information 102 and a second label 300 having human readable information 302 so that a user and/or a machine can easily obtain the desired information regarding the syringe 12 and the contents therein. In one embodiment, the second label 300 may be printed using an inkjet printer so that the human readable information 302 may be in full color.

Referring to FIGS. 15-19, the first label roll 310 and the second label roll 320 provide label rolls that allow the movable label portion 330 between the first label roll 310 and the second label roll 320 to be controlled. In one embodiment, the first label roll 310 is rotatably connected to the first label actuator 312 and the second label roll 320 is rotatably connected to the second label actuator 322. The first label actuator 312 is drivingly connected to the first gear system 316 and the first motor 314. The second label actuator 322 is drivingly connected to the second gear system 326 and the second motor 324. The first label actuator 312, the first gear system 316, and the first motor 314 are movably secured to the first mounting portion 318. The first mounting portion 318 is adapted to secure the gears of the first gear system 316 to the first mounting portion 318 to control the position of the gears of the first gear system 316. In one embodiment, the first mounting portion 318 is formed of sheet metal.

The second label actuator 322, the second gear system 326, and the second motor 324 are movably secured to the second mounting portion 328. The second mounting portion 328 is adapted to secure the gears of the second gear system 326 to the second mounting portion 328 to control the position of the gears of the second gear system 326. In one embodiment, the second mounting portion 328 is formed of sheet metal.

In one embodiment, the first gear system 316 is adapted to provide an arrangement that can be used to increase the strength of the first motor 314. For example, the first gear system 316 is adapted to provide an arrangement that can be used to increase the power, e.g., torque, and/or speed of the first motor 314. In one embodiment, the second gear system 326 is adapted to provide an arrangement that can be used to increase the strength of the second motor 324. For example, the second gear system 326 is adapted to provide an arrangement that can be used to increase the power, e.g., torque, and/or speed of the second motor 324.

In one embodiment, the mounting plate 336 is adapted to secure the components of the second labeling subsystem 18 to the mounting plate 336 to control the position of the components of the second labeling subsystem 18. In one embodiment, the mounting plate 336 is formed of sheet metal.

Figure 17:
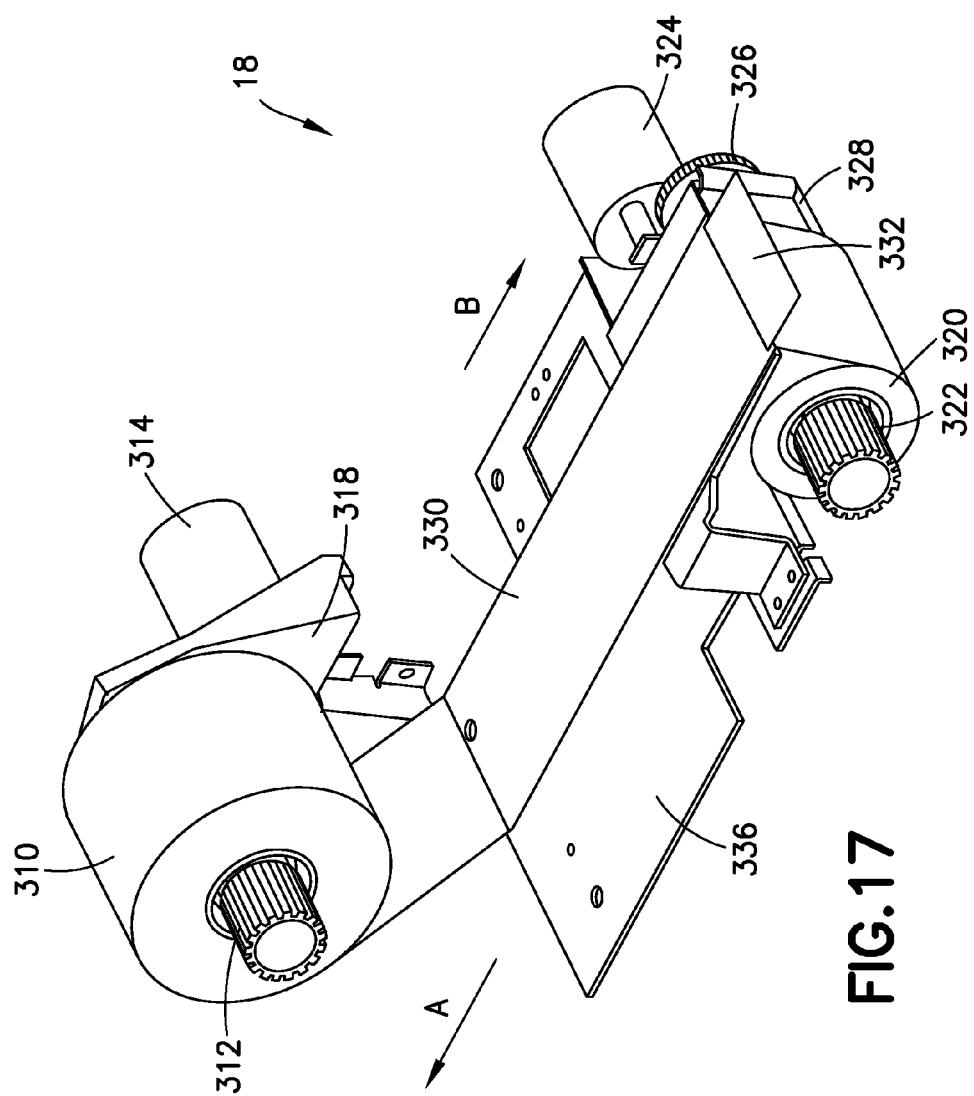
FIG. 17 is a first assembled, perspective view of a second labeling subsystem in accordance with an embodiment of the present invention.
Figure 18:
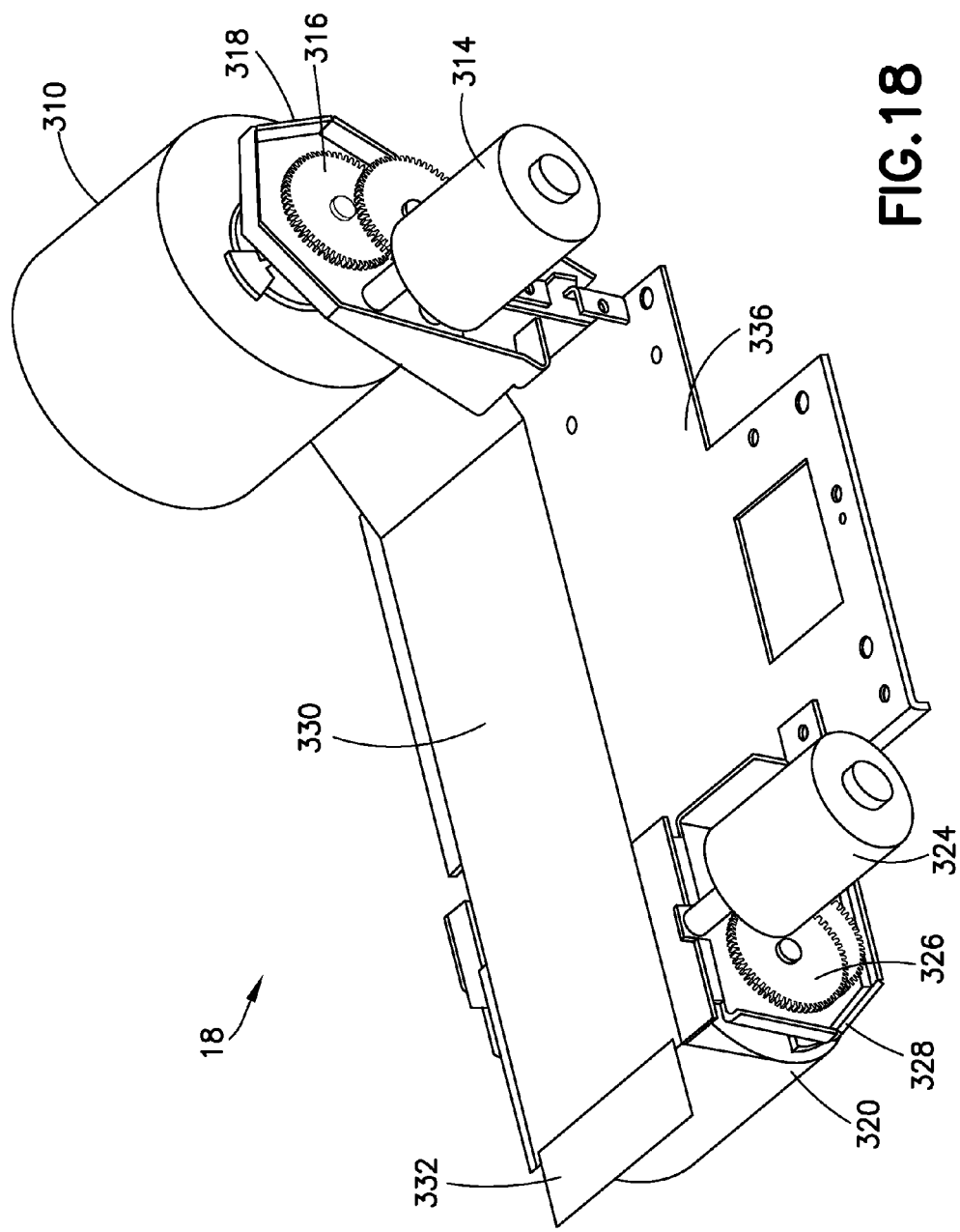
FIG. 18 is a second assembled, perspective view of a second labeling subsystem in accordance with an embodiment of the present invention.
Figure 19:
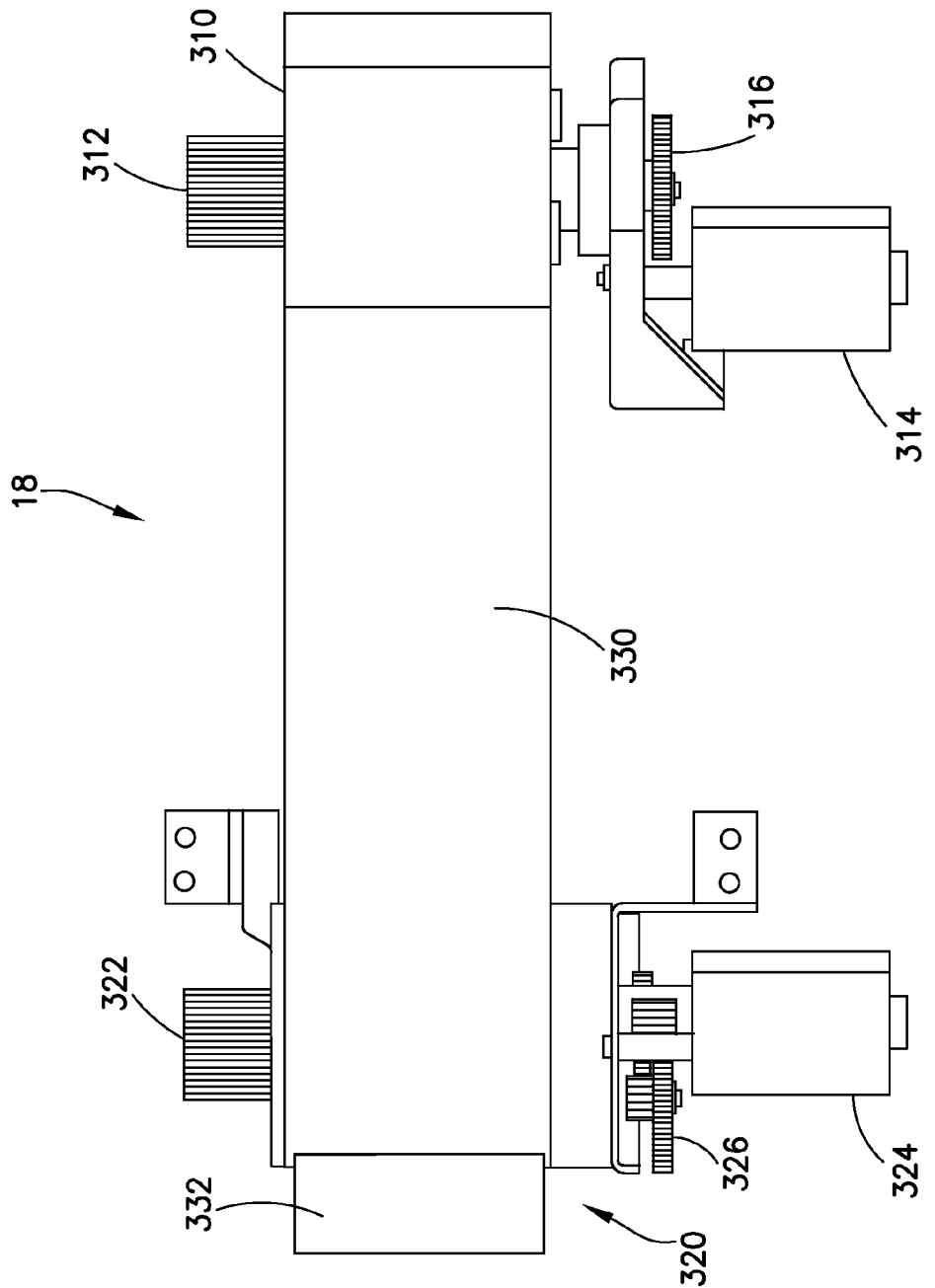
FIG. 19 is a top assembled, perspective view of a second labeling subsystem in accordance with an embodiment of the present invention.

The first motor 314 provides a mechanism to control the torque applied to the first label roll 310 in a first direction generally along arrow A (FIG. 17) and the second motor 324 provides a mechanism to control the torque applied to the second label roll 320 in a second direction generally along arrow B (FIG. 17). The second direction is generally opposite the first direction. In this manner, the first motor 314 and the second motor 324 apply torque to the respective first label roll 310 and the second label roll 320 in opposing directions, thereby placing the movable label portion 330 in tension. In one embodiment, the first motor 314 applies an equal torque force to the first label roll 310 as the second motor 324 applies to the second label roll 320 so that there is no bias in the tensioning force applied to the movable label portion 330. For example, an equal amount of forward tension and rearward tension is applied to the movable label portion 330 so that the net tension force applied to the movable label portion 330 is zero.

By placing the substrate or movable label portion 330 in tension in the manner described above, an actuator or index control system 334 is able to incrementally move the movable label portion 330 back and forth independent of the tension applied to the movable label portion 330. For example, the index control system 334 is adapted to move the label portion 330 in a forward direction and a backward direction. The second labeling subsystem 18 allows for precise control of the movement of the movable label portion 330. For example, the second labeling subsystem 18 allows for independent control of the tension applied to the movable label portion 330, the position of a given point on the movable label portion 330, and the speed at which the movable label portion 330 travels. The second labeling subsystem 18 allows for the precise control of the movement of the movable label portion 330 to control the application of a secondary material to the movable label portion 330, the printing of the human readable information on the movable label portion 330 to form a second label 300, and the cutting of the second label 300 from the movable label portion 330 using a cutting mechanism. The cutting mechanism may include a knife, laser, or water jet printing cutting mechanism.

In one embodiment, the first motor 314 and the second motor 324 are servomotors with closed loop feedback to maintain the proper tension applied to the movable label portion 330. In another embodiment, the first motor 314 and the second motor 324 are brushed DC motors driven by a PWM signal in a torque control mode. In other embodiments, other motors are used to apply tension to the movable label portion 330. For example, the first motor 314 and the second motor 324 may be servo or stepper motors with a closed or open loop feedback to maintain the proper tension applied to the movable label portion 330.

The index control system 334 can include any drive mechanism adapted to move the movable label portion 330 back and forth. In one embodiment, the index control system 334 is a printing mechanism. In other embodiments, other drive mechanisms may be used. In some embodiments, a laser cut printing mechanism, a water jet printing mechanism, or a knife cut printing mechanism may be used.

After the human readable information 302 is printed onto a second label 300, the second label 300 is moved towards an exit area 344 for automatic removal of the backing material 304 of the second label 300. In one embodiment, the second labeling subsystem 18 includes a removal device 332 adapted to automatically remove the backing material 304 of the second label 300. In one embodiment, the removal device 332 comprises a wall that contacts the backing material 304 of the second label 300 as the second label 300 is advanced towards the exit area 344 for removal of the second label 300 from the labeling device 10. In this manner, as the second label 300 advances towards the exit area 344, the removal device 332 contacts the backing material 304 and provides a physical barrier that removes the backing material 304 from the second label 300 as the second label 300 is able to advance beyond the removal device 332. The removal device 332 is dimensioned so that the wall of the removal device 332 contacts the backing material 304 but does not contact the second label 300 so that the second label 300 advances past the removal device 332 while the removal device 332 automatically removes the backing material 304. In one embodiment, the removal device is a wall or edge of sheet metal.

After the second label 300 advances past the removal device 332 and the backing material 304 is removed, the second label 300 advances past the label slot 76 at the front portion 54 of the housing 14 of the labeling device 10 as shown in FIG. 1. In this manner, a user is then able to pick up the second label 300 with one hand and apply the second label 300 having human readable information 302 to the syringe 12 as shown in FIG. 2C. In one embodiment, a cutting mechanism is adapted to automatically cut a portion of the second label 300 for removal of the second label 300 from the labeling device 10.

The user does not have to remove the backing material 304 from the second label 300 because the second labeling subsystem 18 has already automatically removed the backing material 304. Requiring a user such as a medical practitioner to manually remove the backing material 304 from the second label 300 can be a difficult and time consuming process, especially considering the user will be wearing gloves. Also, the user would have to dispose of the backing material 304 every time a second label 300 was printed. Further, the user would have to put down the syringe 12 the second label 300 was meant for, potentially causing confusion if placed near other, similar syringes on a table top or tray.

Referring to FIGS. 1-21, the use of labeling device 10 to print a first label 100 having machine readable information 102 and a second label 300 having human readable information 302 for a syringe will now be described.

Referring to FIG. 2A, a needle 44 is attached to syringe barrel 24 and the needle 44 is used to fill the syringe barrel 24 with a medication from a separate container, such as a vial, prior to use. Once the syringe barrel 24 is filled with a desired medication, the protective cap 46 is attached to the syringe barrel 24 to surround and cover the needle 44 to prevent accidental needle stick injuries. Next, the syringe barrel 24 and protective cap 46 can be placed within the syringe receiving port 104 of the first labeling subsystem 16 of labeling device 10. The syringe 12 is placed within the syringe clamp assembly 106 of the first labeling subsystem 16 with the gripping components 120 in the open position (FIG. 4). The top door 66 can be opened to place the syringe 12 within the labeling device 10 and closed once the syringe 12 is properly placed within the syringe receiving port 104 of the first labeling subsystem 16 of labeling device 10.

Next, the gripping components 120 are moved to the closed position to contact and grip the syringe 12. As the gripping components 120 are moved to the closed position, the gripping components 120 also center the syringe 12 to the proper orientation within the clamp assembly 106 for the automatic application of the first label 100 to the syringe 12. In one embodiment, the drive gear 112 controls the movement of the gripping components 120 between the open position and the closed position via the movable cam connection between the drive gear 112 and the gripping components 120, e.g., cam posts 138, 142, 146 connecting the gripping components 120 and the drive gear at the cam slots 136, 140, 144. In this manner, the syringe clamp assembly 106 securely holds syringe 12 while the label print and apply assembly 108 automatically applies a first label 100 to the luer tip 42 of the syringe 12. Advantageously, the automatic application of the first label 100 to the syringe 12 using labeling device 10 eliminates the potential for misapplication of the first label 100 or human error.

Next, the print and apply state controller 218 of the label print and apply assembly 108 activates the first label print assembly 200 to print a first label 100. After printing of the first label 100, the print and apply state controller 218 activates the label apply assembly 202 to automatically apply the first label 100 to the luer tip 42 of the syringe 12. To facilitate the automatic application of the first label 100 to the syringe 12, the components of the clamp assembly 106 rotate together to rotate the syringe 12 during the automatic application of the first label 100 to the syringe 12. In one embodiment, the syringe 12 is rotated during the automatic application of the first label 100 to the syringe 12 while the first label 100 remains in a stationary position. To ensure the first label 100 is securely applied to the syringe 12, outward movement of the actuation member 268 of the solenoid 266 causes the frame member 264 to pivot such that the roller contact portion 262 can be positioned to contact a portion of the first label 100 as the first label 100 is automatically being applied to the luer tip 42 of the syringe 12. In one embodiment, the first label 100 is of a sufficient length so that as the first label 100 is applied to the luer tip 42 of the syringe 12, the first label 100 wraps around the luer tip 42 and a portion of the first label 100 overlaps itself. In this manner, the first label 100 is securely attached to a luer tip 42 that may have a lubricant or other fluid on it.

As the operation of the printing and automatic application of the first label 100 to the syringe 12 is occurring, the second labeling subsystem 18 can print the second label 300 including human readable information 302 as described above.

As described above, the first motor 314 and the second motor 324 apply torque to the respective first label roll 310 and the second label roll 320 in opposing directions, thereby placing the movable label portion 330 in tension. By placing the movable label portion 330 in tension, an index control system 334 is able to incrementally move the movable label portion 330 back and forth independent of the tension applied to the movable label portion 330. The second labeling subsystem 18 allows for independent control of the tension applied to the movable label portion 330, the position of a given point on the movable label portion 330, and the speed at which the movable label portion 330 travels.

After the human readable information 302 is printed onto a second label 300, the second label 300 is moved towards the exit area 344 for automatic removal of the backing material 304 of the second label 300 via the removal device 332.

After the first label 100 is printed and automatically applied to the luer tip 42 of the syringe 12, a user is able to remove the syringe 12 from the labeling device 10. Next, the user can easily remove the second label 300 from the label slot 76 and position the second label 300 on the syringe 12. Advantageously, the user does not have to remove the backing material 304 from the second label 300 as the second labeling subsystem 18 has already automatically removed the backing material 304. Next, the syringe 12 may be used to administer a medication, as is known in the art.

The labeling device 10 provides for a syringe 12 having a first label 100 including machine readable information 102 and a second label 300 including human readable information 302 as shown in FIG. 2C. In this manner, the labeling device 10 provides a first label 100 having machine readable information 102 and a second label 300 having human readable information 302 so that a user and/or a machine can easily obtain the desired information regarding the syringe 12 and the contents therein. The machine readable information 102 on the first label 100 may be scanned to determine the contents of the syringe 12 at any time using the same scanner used to scan drug vials. For example, in one embodiment, the scanner 20 located on the front portion 54 of the housing 14 of the labeling device 10 can be used to scan the machine readable information 102 on the first label 100 to determine the contents of the syringe 12 at any time.

A syringe 12 having a first label 100 including machine readable information 102 and a second label 300 including human readable information 302 provides encoded syringes that can be utilized along with the EMR system of a hospital to track drug administration, check for potential allergies or drug interactions, and/or other important information, all without the need for human intervention.

The labeling device 10 is envisioned to be a part of a larger system solution to combat medication errors. For example, the labeling device 10 works to eliminate the following adverse effects that can be caused by medication errors: (1) unclear syringe contents from unlabeled or poorly labeled syringes; (2) allergic reactions; (3) drug interactions; and (4) poor record keeping, e.g., which drugs were administered, concentration, and/or quantity of drug.

It is envisioned that other potential methods may be used with the labeling device 10 of the present disclosure for linking each syringe to specific information regarding the drugs contained within the syringe and patient information.

For example, the machine readable information 102 on the first label 100 may comprise any mechanism for transmitting specific information regarding the drugs contained within the syringe and patient information. In one embodiment, a radio-frequency identification (RFID) system may be used. Empty syringes may come preloaded with an RFID or an RFID label would be applied. The labeling device 10 would read the code and add that information to a database, tying the syringe to the drug and concentration the syringe contains as well as for which patient it was intended. In such a system, it would also be possible to add information to the unique RFID from a database.

In one embodiment, a near field communication system may be used. Such a system would include similar implementation to the RFID system discussed above.

In one embodiment, a laser marking system may be used. The labeling device 10 may contain a laser capable of marking the syringe directly, or a blank label on the syringe, with the necessary barcode information. Such a system may or may not require custom formulation of syringe material to incorporate photosensitive materials for use with the laser.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A labeling device for a syringe, comprising:
a first labeling subsystem adapted to print a first label comprising machine readable information; and
a second labeling subsystem adapted to print a second label comprising human readable information,
wherein the first labeling subsystem includes a label applicator adapted to automatically apply the first label to a portion of the syringe,
wherein the label applicator is adapted to hold the first label position as the syringe is rotated about its cylindrical axis during the automatic application of the first label to the syringe, and wherein the second labeling subsystem automatically applies the second label to another portion of the syringe simultaneously with the first labeling subsystem automatically applying the first label to the portion of the syringe.

2. The labeling device of claim 1, wherein the label applicator automatically applies the first label to a luer tip of the syringe.

3. The labeling device of claim 1, wherein the machine readable information is a barcode indicating a content or quality of the syringe.

4. The labeling device of claim 1, wherein the machine readable information and the human readable information each indicate a content or quality of the syringe.

5. The labeling device of claim 1, further comprising a housing, wherein the first labeling subsystem and the second labeling subsystem are each provided within the housing.

6. The labeling device of claim 1, further comprising a scanner adapted to scan a container having a medication therein to retrieve medication information about the medication contained in the container.

7. The labeling device of claim 6, further comprising a touchscreen interface adapted to display the medication information.

8. The labeling device of claim 6, wherein at least one of the first label and the second label include at least a portion of the medication information.

9. A labeling subsystem for a labeling device for a syringe, comprising:
a clamp assembly adapted to hold the syringe;
a printer adapted to print a first label comprising machine readable information; and
a label applicator assembly adapted to automatically apply the first label to a portion of the syringe,
wherein the clamp assembly is adapted to rotate the syringe about its cylindrical axis while the label applicator assembly automatically applies the first label to a portion of the syringe,
wherein the clamp assembly includes a plurality of jaws movable between an open position, in which the jaws do not restrain the syringe, and a closed position, in which the jaws hold the syringe, and
wherein with the plurality of jaws in the closed position, the clamp assembly including the plurality of jaws is adapted to rotate together about the cylindrical axis of the syringe to rotate the syringe while the label applicator assembly automatically applies the first label to a portion of the syringe.

10. The labeling subsystem of claim 9, wherein the label applicator assembly automatically applies the first label to a luer tip of the syringe.

11. The labeling subsystem of claim 10, wherein the clamp assembly includes a syringe alignment component adapted to position the syringe within the clamp assembly, wherein the syringe alignment component comprises a central aperture adapted to receive the luer tip of the syringe therethrough.

12. The labeling subsystem of claim 9, wherein the clamp assembly includes a drive gear and movement of the jaws between the open position and the closed position is controlled by a movable cam connection between the jaws and the drive gear.

13. The labeling subsystem of claim 9, further comprising a print and apply state controller that activates the printer to print the first label and activates the label applicator assembly to automatically apply the first label to a portion of the syringe.

14. The labeling subsystem of claim 9, wherein the label applicator assembly includes an optical syringe alignment unit having a first camera for locating a position of the syringe within the clamp assembly.

15. The labeling subsystem of claim 14, wherein the optical syringe alignment unit further includes a second camera for viewing the machine readable information on the first label.

16. The labeling subsystem of claim 9, wherein the label applicator assembly includes a pinch roller mechanism for exerting a force on the first label as the first label is automatically applied to the syringe to ensure that the first label is securely applied to the syringe.

17. A labeling subsystem for a labeling device for a syringe, comprising:
a clamp assembly adapted to hold the syringe;
a printer adapted to print a first label comprising machine readable information; and
a label applicator assembly adapted to automatically apply the first label to a portion of the syringe,
wherein the clamp assembly is adapted to rotate the syringe about its cylindrical axis while the label applicator assembly automatically applies the first label to a portion of the syringe, wherein the label applicator assembly automatically applies the first label to a luer tip of the syringe, and
wherein the clamp assembly includes a syringe alignment component adapted to position the syringe within the clamp assembly, wherein the syringe alignment component comprises a central aperture adapted to receive the luer tip of the syringe therethrough.

\* \* \* \* \*